US008969815B2

(12) United States Patent
Caruba et al.

(10) Patent No.: US 8,969,815 B2
(45) Date of Patent: Mar. 3, 2015

(54) POWER DISTRIBUTION IN MR-PET IMAGING SYSTEM INTEGRATION

(75) Inventors: James Frank Caruba, Bartlett, IL (US); Darryl Hrdina, Mount Prospect, IL (US); Grant Arthur Albert, Hoffman Estates, IL (US); Paul Finlon, Palatine, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 716 days.

(21) Appl. No.: 13/186,880

(22) Filed: Jul. 20, 2011

(65) Prior Publication Data

US 2012/0019064 A1 Jan. 26, 2012

Related U.S. Application Data

(60) Provisional application No. 61/366,267, filed on Jul. 21, 2010, provisional application No. 61/366,272, filed on Jul. 21, 2010.

(51) Int. Cl.

| G01T 1/164 | (2006.01) |
| G01T 1/166 | (2006.01) |
| A61B 5/05 | (2006.01) |
| G01V 3/00 | (2006.01) |
| G01R 33/28 | (2006.01) |
| G01R 33/48 | (2006.01) |
| A61B 6/00 | (2006.01) |
| A61B 5/055 | (2006.01) |
| A61B 6/03 | (2006.01) |

(52) U.S. Cl.
CPC .............. *G01R 33/28* (2013.01); *G01R 33/481* (2013.01); *A61B 6/5235* (2013.01); *A61B 5/055* (2013.01); *A61B 6/037* (2013.01)

USPC ............ 250/363.03; 250/363.04; 250/363.05; 600/407; 324/307

(58) Field of Classification Search
CPC ....... G01R 33/481; G01R 33/28; A61B 5/055
USPC ........... 250/363.03, 363.04, 363.05; 600/407, 600/408; 324/307
See application file for complete search history.

(56) References Cited

U.S. PATENT DOCUMENTS

| 5,672,877 A | 9/1997 | Liebig et al. |
| 2005/0113667 A1 | 5/2005 | Schlyer et al. |
| 2007/0102641 A1 * | 5/2007 | Schmand et al. ........ 250/363.03 |

(Continued)

FOREIGN PATENT DOCUMENTS

WO  WO2009/147551 A1 * 10/2009  .............. H02M 7/23

OTHER PUBLICATIONS

"Selecting a Power System Architecture" p. 1-14 (Jun. 2006), available at http://www.cps.fi/Library/Pwr_Syst_Architecture.pdf.*

*Primary Examiner* — David J Makiya
*Assistant Examiner* — Kenneth J Malkowski
(74) *Attorney, Agent, or Firm* — Peter Kendall

(57) ABSTRACT

An integrated magnetic resonance (MR) and positron emission tomography (PET) system includes an MR scanner including a magnet that defines an opening in which a subject is positioned, a set of PET detectors disposed about the opening, a plurality of data processing units each electrically connected with a respective one or more of the PET detectors of the set of PET detectors, and a plurality of power supply modules, each power supply module being operable to generate a DC power supply for different groups of one or more of the data processing units. Each power supply module is discrete from the other power supply modules.

32 Claims, 12 Drawing Sheets

(56) References Cited

U.S. PATENT DOCUMENTS

| | | |
|---|---|---|
| 2007/0130554 A1 | 6/2007 | Caruba |
| 2009/0072151 A1* | 3/2009 | Zhang et al. ............. 250/363.03 |
| 2009/0093710 A1* | 4/2009 | Levin et al. ................... 600/411 |
| 2010/0076300 A1 | 3/2010 | Arseneau et al. |
| 2011/0291657 A1* | 12/2011 | Davila et al. ................... 324/322 |
| 2012/0083936 A1* | 4/2012 | Van Vliet et al. ............. 700/293 |

* cited by examiner

POWER DISTRIBUTION IN MR-PET IMAGING SYSTEM INTEGRATION

CROSS-REFERENCES TO RELATED APPLICATIONS

This application claims the benefit of U.S. provisional applications entitled "Power Distribution for Hybrid Imaging," filed Jul. 21, 2010, and assigned Ser. No. 61/366,267, and entitled "Board-Level Partitioning for Hybrid Imaging," filed Jul. 21, 2010, and assigned Ser. No. 61/366,272, the entire disclosures of which are hereby incorporated by reference.

BACKGROUND

The present embodiments relate to integration of imaging systems, specifically magnetic resonance (MR) imaging and positron emission tomography (PET) systems.

PET may be combined with another imaging modality in a multimodality system. Such multimodality imaging systems may have diagnostic and business value. Both PET/computed tomography (CT) and single photon emission computed tomography (SPECT)/CT multimodality imaging systems allow scans to be performed back-to-back or in a same coordinate system and with similar timing. The axial fields of view of the individual modalities are as close together as possible in order to minimize the impact of patient motion and increase spatial correlation of the respective data sets.

Another hybrid example is a brain scan PET system integrated with a magnetic resonance (MR) system. In order for the MR and PET fields of view to overlap, the PET detectors are placed as an insert in front of the body coil. The MR body coil is used to excite the molecules of the patient by delivering an RF burst. The MR switches into a receive mode, after delivery of the RF burst, and detects RF signals emitted from the patient. The signal-to-noise ratio of the MR received signal is an important aspect of MR imaging. The signal-to-noise ratio is important enough that a typical MR system is enclosed in a radio frequency (RF) cabin that suppresses RF signals, such as by 100 dB, for both external signals entering the RF cabin and internal signals exiting the RF cabin.

Electromagnetic interference (EMI) and electromagnetic compatibility (EMC) between the MR and PET subsystems is one of the dominant technical challenges facing MR/PET integration. The MR subsystem is extremely sensitive to any RF emissions from the PET subsystem, near the hydrogen spin frequency (e.g., roughly 123 MHz+/−500 KHz for a 3 Tesla system). Likewise, the PET front end is extremely vulnerable to the RF emissions from the MR subsystem. Coincidence windows of 4-10 nS are typical of non-time-of-flight PET scanners, which corresponds with a PET signal chain stable to 100 pS. For the brain scan PET/MR system, the detector signals are routed out of the RF cabin to avoid EMI and EMC issues with the MR subsystem. Outside the cabin, the signals are amplified and filtered. However, the length of the cabling may have detrimental effects on signal integrity and timing precision for the PET subsystem. The volume and weight of the cabling may introduce other complications, including performance limitations through restrictions on the number of PET detectors in the integrated system.

SUMMARY

By way of introduction, the embodiments described below include systems, devices, and methods for supporting the integration of components of a magnetic resonance (MR) subsystem and a positron emission tomography (PET) subsystem. A plurality of data processing units are provided with power via a modular power distribution architecture.

In a first aspect, an integrated magnetic resonance (MR) and positron emission tomography (PET) system includes an MR scanner including a magnet that defines an opening in which a subject is positioned, a set of PET detectors disposed about the opening, a plurality of data processing units each electrically connected with a respective one or more of the PET detectors of the set of PET detectors, and a plurality of power supply modules, each power supply module being operable to generate a DC power supply for different groups of one or more of the data processing units. Each power supply module is discrete from the other power supply modules.

In a second aspect, an integrated magnetic resonance (MR) and positron emission tomography (PET) system includes an MR scanner including a magnet that defines an opening in which a subject is positioned, a set of PET detectors disposed between the magnet and the opening, a plurality of data processing units each in communication with a respective one or more of the PET detectors of the set of PET detectors, and a power distribution system including a plurality of power supply modules, each power supply module being configured to generate a DC power supply for a respective one of the data processing units. Each data processing unit is in galvanic isolation from each other data processing unit of the plurality of data processing units.

In a third aspect, a method of integrating magnetic resonance (MR) and positron emission tomography (PET) imaging includes generating a respective DC power supply for each PET data processing unit of a plurality of PET data processing units disposed in an RF cabin, filtering each DC power supply with a respective power filter of a plurality of power filters disposed at an interface to the RF cabin, and carrying each filtered DC power supply in the RF cabin to a respective PET data processing unit of the plurality of PET data processing units.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE PRESENTLY PREFERRED EMBODIMENTS

Figure 1:
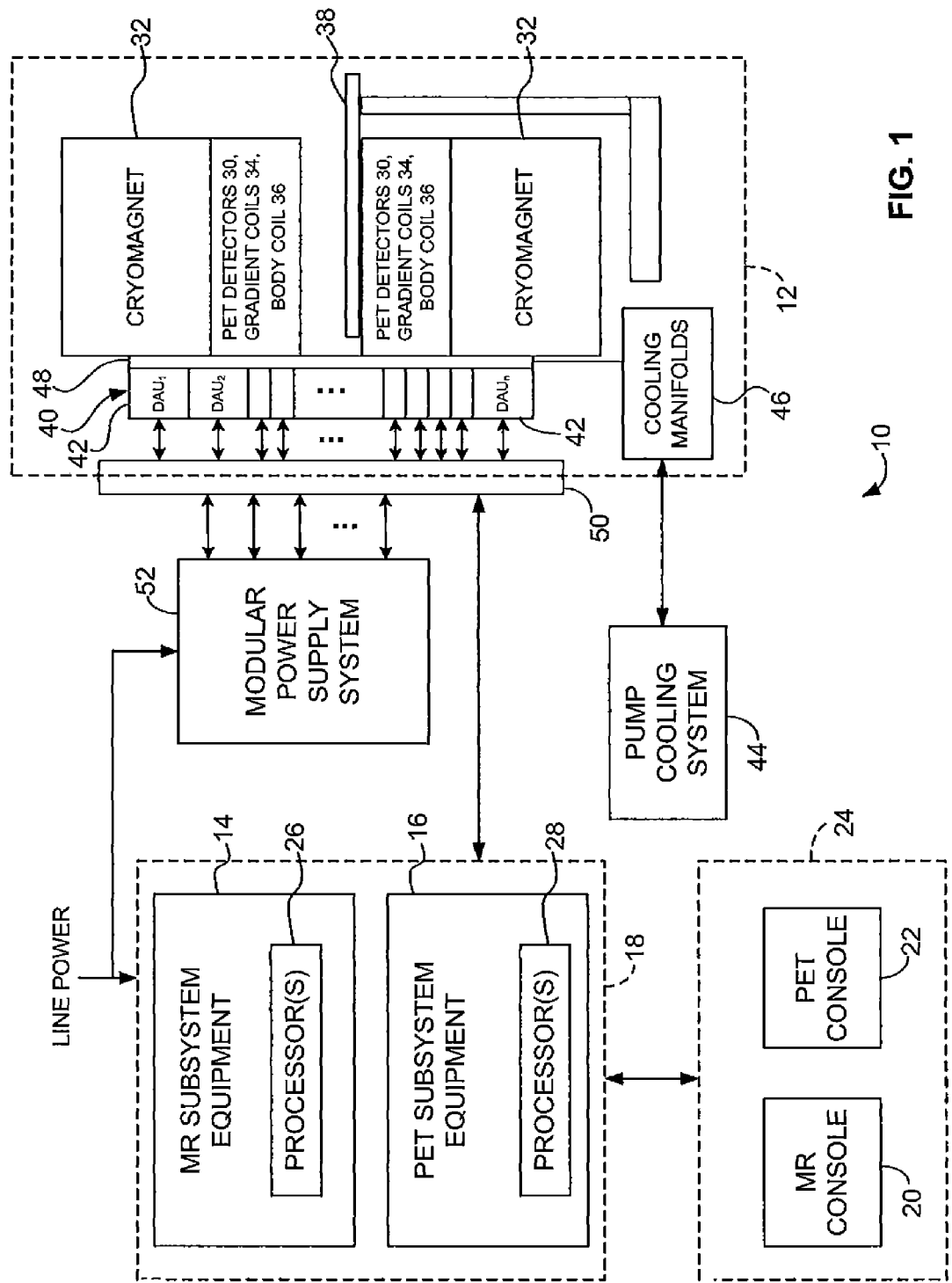
FIG. 1 is a block diagram of an example embodiment of an integrated MR/PET imaging system.

An integrated PET/MR system is provided for whole body or other imaging. PET and MR image data may be acquired simultaneously with overlapping or the same volumetric fields of view. Signals from PET detectors, such as avalanche photodiodes, are filtered, amplified, digitized, and otherwise processed inside the RF cabin. Addressing these data processing functions inside the RF cabin may allow the length of the interconnects between PET detectors and PET digitization electronics to be minimized. Such processing of the PET detector signals may maintain PET signal data integrity, improve PET data timing precision, and/or otherwise reduce signal losses or other distortion. Such processing may reduce cabling requirements, relative to integrated systems that process the PET detector signals outside the RF cabin.

An integrated MR/PET imaging system includes a number of PET subsystem components disposed within an MR environment (e.g., an RF cabin). Data processing and other aspects of the PET subsystem occur within the RF cabin despite the strong magnetic fields presented by the MR environment and despite the intolerance of the MR subsystem for RF noise. The PET subsystem includes a number of data processing units configured with an RF shield housing for compatibility with the main magnet, gradient, and RF excitation fields of the MR subsystem. The RF shield housing of each data processing unit is also configured to block the RF emissions of the enclosed electronics and avoid interfering with the MR imaging. Locating these PET subsystem components inside the RF cabin may allow the data processing and other PET operations to be implemented in close proximity to the PET detectors. The integrated MR/PET imaging system may include a thermal management apparatus to manage the heat generated by the PET subsystem components within the RF cabin.

The PET subsystem may be configured in a modular architecture. Each data processing unit may be discrete from the other data processing units. Each data processing unit may be galvanically isolated from the other data processing units via a modular power distribution system. Two or more data processing units are provided, such as tens or hundreds. In alternative embodiments, a single data processing unit and housing are provided.

The data processing units of the PET subsystem may be disposed in a variety of arrangements within the RF cabin. Deployment options include near the MR scanner or main magnet (e.g., near the magnet bore) in a symmetrical star, near the MR scanner or magnet in one or more clusters, alongside the MR scanner or magnet in symmetrical columns, or spaced from the MR scanner within the RF cabin. Although described in connection with a number of examples in which the data processing units are located adjacent the MR scanner or main magnet, the data processing units may be disposed in a variety of locations within the RF cabin, including, for example, some locations closer to an RF filter plate that provides an interface with the RF cabin. The disclosed systems may include a gantry or other apparatus for adjusting the location of the data processing units and/or other components of the PET subsystem within the RF cabin. The spacing between the data processing units and the MR scanner, main magnet, or magnet opening (e.g., bore) may be fixed or adjusted.

The disclosed systems and methods are not limited to use with any particular MR subsystem or primary magnet type. The MR subsystem need not include a cryomagnet or superconducting or other electromagnet. The MR subsystem may have a tunnel or open configuration. Other characteristics of the MR subsystem may also vary, including the construction and components of the RF cabin.

FIG. 1 shows a hybrid magnetic resonance (MR) and positron emission tomography (PET) system 10. The hybrid PET/MR system 10 includes PET and MR portions or subsystems. Only parts of the PET subsystem and parts of the MR subsystem are shown. Additional, different, or fewer components may be provided. The MR and PET subsystems include scanners or scanning components located within an RF cabin 12 that defines an imaging or scanning environment for each subsystem. The RF cabin 12 may be a room or other enclosure configured with one or more RF shields to reduce RF noise within the environment. The RF cabin 12 may be a volume of any desired shape or size isolated by a Faraday cage. The construction and other characteristics of the RF cabin 12 and the RF shields of the RF cabin 12 may vary considerably.

The PET and MR subsystems may include a number of components located outside of the RF cabin 12. The system 10 includes MR subsystem equipment 14 and PET subsystem equipment 16, which may be located in respective equipment cabinets or other enclosures. In this example, separate cabinets for the equipment 14, 16 are located in an equipment room 18 outside of the RF cabin 12. The system 10 includes consoles or other user interfaces 20, 22 for the MR and PET subsystems, respectively, which may be located in an operator or user control room outside of the RF cabin 12. Each console 20, 22 is in communication with the subsystem equipment 14, 16 to control the operation of the system 10. Different divisions of the parts of the MR and/or PET subsystems within and outside of the RF cabin 12 may be provided.

The subsystem equipment 14, 16 may include any number of respective processors 26, 28, configured to control and communicate with the scanning components of the system 10 inside the RF cabin 12. The processors 26, 28 may include, for instance, a coincidence processor for the PET subsystem. Other processors may be configured to provide acquisition control for the MR and PET subsystems or PET image reconstruction. The subsystem equipment 14, 16 may include a number of devices for developing the imaging data, such as RF receivers for the MR subsystem. The subsystem equipment 14, 16 may also include one or more components or devices directed to DC and other power distribution to these devices. In this example, the subsystem equipment receives line power (e.g., 480 Volts, three phase).

Inside the RF cabin 12, the MR and PET scanners or image capture components may be integrated into a single freestanding scanner unit to be occupied by a subject to be imaged. A number of components of the scanner unit may be disposed within a common housing. For example, the scanning components of the system 10 shown in FIG. 1 may be packaged in a single common enclosure. The single common enclosure may include a plurality of housings or shields that fit together or adjacent to each other. In other embodiments, the scanning components of the integrated PET/MR system 10 are disposed in multiple housings or separate freestanding units.

The scanning components of the PET subsystem include a set of PET detectors 30, which may be, for instance, whole body detectors. Additional, different, or fewer PET-related components may be provided. Any now known or later developed PET imaging system components may be used with the modifications discussed herein. The PET detectors 30 are coupled to and in communication with other parts of the PET subsystem in a manner that allows the MR and PET subsystems to be integrated while minimizing image data distortion or other loss. Such connections with the PET subsystem are directed to a variety of functions, including, for instance, power supply, control and other data communication, image data processing, system clock signals, and cooling.

In nuclear medicine imaging, such as PET, radioactive tracer isotopes, or radiopharmaceuticals, are taken internally, for example intravenously or orally. As the radioisotope undergoes positron emission decay (also known as positive beta decay), the radioisotope emits a positron, an antiparticle of the electron with opposite charge. The emitted positron travels in tissue for a short distance, during which time the positron loses kinetic energy, until the positron decelerates to a point where the positron interacts with an electron. The encounter annihilates both electron and positron, producing a pair of annihilation (gamma) photons moving in approximately opposite directions. These events are detected when the gamma radiation reaches a crystal scintillator in the PET detector 30, creating a burst of light which is detected by photomultiplier tubes or silicon avalanche photodiodes (Si APD) in the PET detector 30. The PET detectors 30 capture data representing the radiation emitted, directly or indirectly, by the radiopharmaceuticals. The PET subsystems forms images from the captured data.

The MR scanning components in the RF cabin 12 include a main magnet 32, gradient coils 34, a body coil 36, and a patient bed 38. Additional, different, or fewer components may be provided. Other parts of the MR subsystem may be provided within a same housing shared by these MR components, within a same room (e.g., within the RF cabin 12), or with the other MR subsystem equipment 14. The other scanning parts of the MR subsystem may include local coils, cooling systems, pulse generation systems, image processing systems, and user interface systems. Any now known or later developed MR imaging system may be used with the modifications discussed herein. The location of the different components of the MR subsystem (e.g., inside or outside the RF cabin) may vary, with the image processing, tomography, power generation, and user interface components being, for instance, outside the RF cabin 12. Power cables, cooling lines, and communication cables connect the pulse generation, magnet control, and detection systems within the RF cabin 12 with the components outside the RF cabin 12 through a filter plate.

The configuration of the main magnet 32 may vary. The main magnet may be a cryomagnet (e.g., a superconducting or other electromagnet) or a fixed or permanent magnet. The main magnet 32 and other MR scanning components may be configured to have a tubular bore, a laterally open examination subject bore, or any other opening defining a field of view. The patient bed 38 (e.g., a patient gurney or table) supports an examination subject such as, for example, a patient. The patient bed 38 may be moved into the examination subject bore in order to generate images of the patient. In one embodiment, a local coil arrangement for acquiring signals from a local region (e.g., the head) may be placed on or adjacent to the patient. Received signals may be transmitted by the local coil arrangement via, for example, coaxial cable or radio link (e.g., via antennas) for image generation.

In order to examine the patient using the MR portion, different magnetic fields are temporally and spatially coordinated with one another for application to the patient. The main magnet 32 generates a strong static main magnetic field B0 in the range of, for example, 0.2 Tesla to 3 Tesla or more. The main magnetic field B0 is approximately homogeneous in the field of view. The main magnetic field B0 may extend throughout the RF cabin 12. Different regions within the RF cabin 12 may be subjected to stronger or weaker magnetic fields. For example, the magnetic field B0 may be weaker in regions near the ends of the main magnet 32, but such regions may remain sufficiently within the magnetic field to give rise to challenges for integrating the PET subsystem components into the RF cabin.

The MR subsystem uses the strength of the main magnetic field B0 to align the nuclear magnetization (i.e., spins) of atomic nuclei in the subject (e.g., hydrogen atoms in water). High-field systems (e.g., 1.5 T or 3 T and more) may be used to improve the signal-to-noise ratio. Radio frequency (RF) fields are used to systematically alter the alignment of this magnetization. The nuclear spins of atomic nuclei of the patient are excited via magnetic RF excitation pulses that are transmitted via an RF antenna, shown in FIG. 1 in simplified form as the body coil 36, and/or possibly a local coil arrangement. The RF excitation pulses are generated, for example, by a pulse generation unit controlled by a pulse sequence control unit. After being amplified using an RF amplifier, the RF excitation pulses are routed to the body coil 36 and/or local coils. The excitation causes the nuclei to produce a rotating magnetic field detectable by the MR scanner.

The response to the RF excitation pulses may be manipulated by additional magnetic fields applied by the gradient coils 34 to build up enough information to construct an image of the body. The gradient coils 34 radiate magnetic gradient fields in the course of a measurement in order to produce selective layer excitation and for spatial encoding of the measurement signal. The gradient coils 34 are controlled by a gradient coil control unit that, like the pulse generation unit, is connected to the pulse sequence control unit.

The signals emitted by the excited nuclear spins are received by the body coil 36 and/or at least one local coil arrangement. The body coil 36 may have a one-piece construction or include multiple coils. The signals are in a given frequency band. For example, the MR frequency for a 3 Tesla system using the spin of hydrogen is about 123 MHz+/−350 KHz. Different center frequencies and/or bandwidths may be used. The voltage induced in the body coil 36 may be amplified by a low-noise preamplifier (e.g., LNA, preamp) and forwarded to receive electronics. A switching array (e.g., BCCS) may be installed between the receive antennas and the receivers. The switching array routes the currently active receive channels (e.g., the receive channels currently lying in the field of view of the magnet) to the receivers present. More coil elements may then be connected than the number of receivers present to allow, in the case of whole-body coverage, only the coils located in the field of view or in the homogeneity volume of the magnet to be read out.

In some MR tomography procedures, images having a high signal-to-noise ratio (SNR) may be recorded using local coil arrangements (e.g., loops, local coils). The local coil arrangements (e.g., antenna systems) are disposed in the immediate vicinity of the examination subject on (anterior) or under (posterior) or in the patient. The received signals are amplified by associated radio-frequency preamplifiers, transmitted in analog or digitized form, and processed further and digitized by a receiving unit. The recorded measured data is stored in digitized form as complex numeric values in a k-space matrix. An associated MR image of the examination subject may be reconstructed using a multidimensional Fourier transform from the k-space matrix populated with values. For a coil that may be operated both in transmit and in receive mode, such as the body coil 36 and/or the local coil, correct signal forwarding is controlled using an upstream-connected duplexer.

From the measured data, an image processing unit in the MR subsystem equipment 14 generates an image. The image is displayed to a user via the operator console 20 and/or stored in a memory unit. A central computer unit in the MR subsystem equipment cabinet may control the individual system components.

Combinations of medical imaging techniques, so-called "hybrid modalities," may provide a high local resolution modality (e.g., MR imaging) with a modality with high sensitivity (e.g., PET). Both detailed anatomy and functional information may be provided in spatial alignment and without errors introduced by temporal discontinuity. While the MR-PET combination may present imaging advantages, simultaneous operation of PET and MR subsystems also presents an interoperability risk if the electronic and electromagnetic aspects of the subsystems interfere with one another. For example, performance of the MR subsystem may be detrimentally affected if the PET subsystem performs digital sampling and other data processing at a location or in a manner where those activities interfere with the MR receivers at the spin frequencies of the MR subsystem, e.g., 123.212 MHz for 3 T Hydrogen. For example, RF signals (either directly, or mixed with other signals) from the clocks used in PET sampling and/or data processing may interfere with the operation of the MR receivers.

Notwithstanding these risks, the design architecture of the system 10 places PET sampling (or digitization) and/or other electronics inside the RF cabin 12 to be near the PET detectors 30. The PET detectors 30 are positioned inside of the magnet 32, e.g., within the magnet bore or other opening. The PET detectors 30 are arranged individually or in groups. The location and configuration of the PET detectors 30 relative to the MR components inside of the magnet 32 may vary. Interference in the signal chain may be introduced by this positioning. By being within the RF cabin 12, the PET detectors 30 are within the magnetic field generated by the magnet 32. Being within the core of the magnet 32, the PET detectors 30 are subjected to similar B0 magnetic field strength and uniformity as the patient. With the PET sampling and other data processing components inside the RF cabin 12, the interconnect distance between the PET detectors and PET digital sampling and data processing components is minimized or reduced as compared to placement of the processing components outside the RF cabin 12. This positioning of the data processing components of the PET subsystem within the RF cabin 12 removes a potential source of signal distortion or loss for the PET subsystem.

The digitization electronics of the PET subsystem include an array 40 of data processing units 42 of the system 10 disposed in the RF cabin 12. Each processing unit 42 may be configured as, or include, a data acquisition unit (DAU) configured to acquire the PET detector signals for digitization and other processing. Each DAU 42 in the array ($DAU_1$ through $DAU_n$) 40 may be disposed within a discrete housing or other enclosure separate from the other units 42 as well as from the scanning components inside the RF cabin 12. As described below, it may be useful to dispose the DAU array 40 near the PET detectors 30 to minimize signal distortion or other loss. The DAU array 40 may be mounted on, adjacent to, or otherwise proximate to the scanning components of the system 10. The DAU array 40 may alternatively or additionally be spaced from the scanning components. In some cases, the spacing may be adjustable. In other alternative embodiments, a single housing is provided for all of the DAUs 42 or for one DAU.

The heat generated from the DAU array 40 is removed from the RF cabin 12 via a cooling system 44 in communication with one or more cooling distribution networks 46. The cooling system 44 may include a pump for distributing water or other coolant through pipes of the distribution network 46. The distribution network 46 may include inlet and outlet manifolds. The coolant may be distributed to one or more cooling interfaces 48 in thermal communication with the DAU array 40, such as through metallic blocks or a block in contact with the housings of the DAU array 40. The cooling system 44 may provide any one or more fluids other than water (e.g., air) to remove heat from the RF cabin 12.

Connections for power and data communications with the DAU array 40 are provided via a filter plate 50 disposed along a wall or other boundary of the RF cabin 12. The filter plate 50 may include a set of RF-tight interfaces that allow power and data connections to enter the RF cabin 12 with little introduction of noise. Each interface may include a filter configured to remove from each power line any frequency components that would interfere with the operation of the MR scanner. In this example, a respective power connection and, thus a respective filter, is provided for each DAU 42 in the array 40. The filter plate 50 may include a separate interface (or set of interfaces) for the data and control signals for the DAU array 40, which may be carried via fiber optic links The optical signals carried by the fiber optic links may be multiplexed either inside or outside the RF cabin 12. The RF filter plate 50 may include any one or more interfaces for other signals, including, for instance, a clock signal. The configuration, construction, and other characteristics of the filter plate 50 may vary.

The electronics of the DAU array 40 are powered by DC power provided via a power supply system 52. The power supply system 52 is located outside of the RF cabin 12, and is coupled to the RF filter plate 50 to provide the DC and other power via the filters to the scanning components in the RF cabin 12. The DC power may be developed from single-phase line power (e.g., 230 Volts). The power supply system 52 may be modular. In one example, separate DC power signals are developed for each filter. An alternative embodiment may include power distribution equipment inside the RF cabin 12, such that the filtering provided by the filter plate 50 may only act upon a single DC power line. Yet another alternative embodiment may integrate one or more components of the power supply system 52 with the PET subsystem equipment 16.

Figure 2:
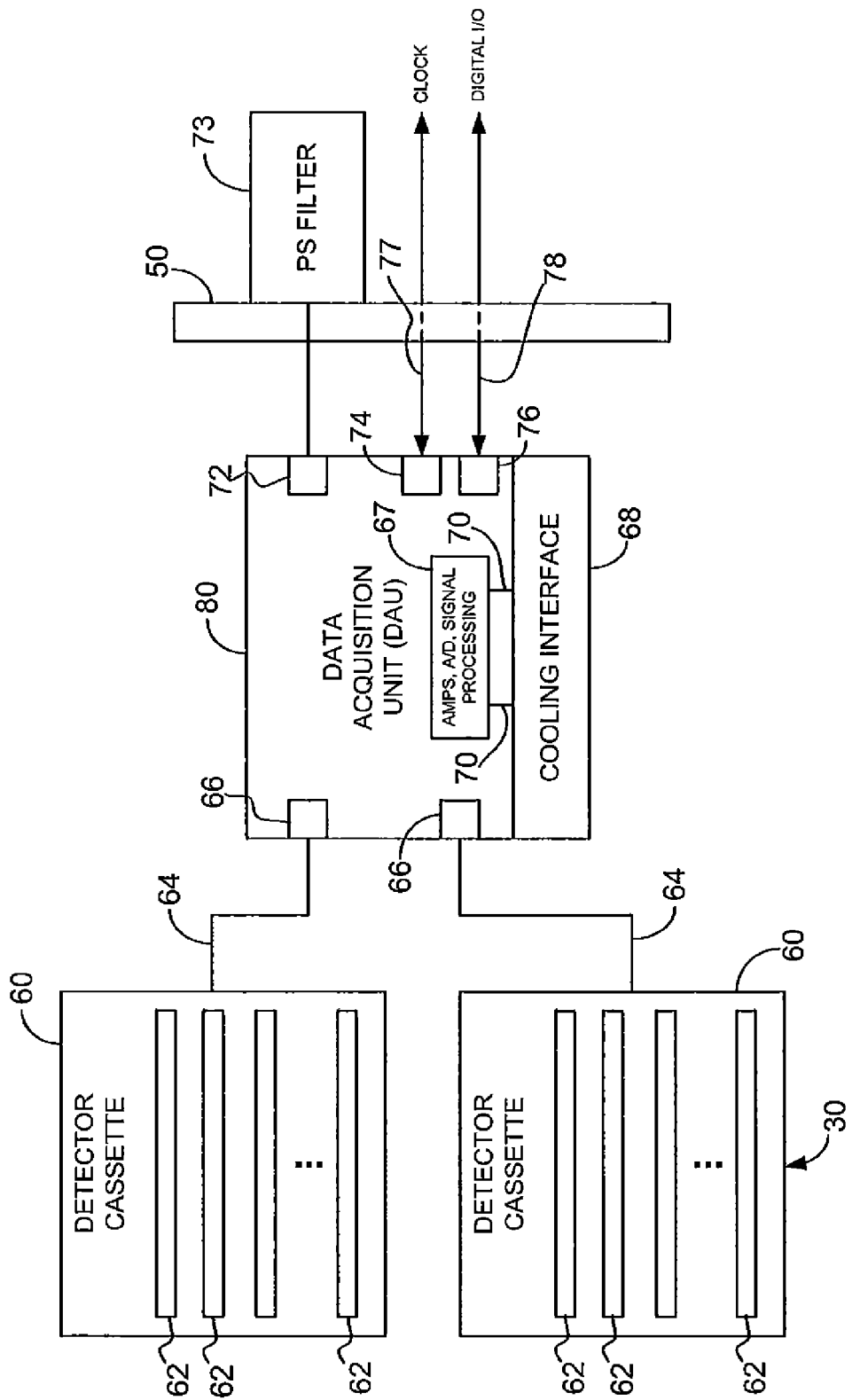
FIG. 2 is a block diagram of data acquisition components of a PET subsystem within an RF cabin according to one embodiment.

FIG. 2 shows the PET subsystem components in the RF cabin in greater detail. Each DAU 42 may be configured to support the processing of the signals from the PET detectors 30 within the RF cabin. Each DAU 42 may include (1) an interface for one or multiple PET block detector cassettes, (2) a thermally conductive interface for heat removal, (3) a filtered power interface, and (4) optical and/or RF interfaces for clock distribution, command and control communications, and communications for event and general purpose data output. Each of these and other aspects of the DAU 42 may allow the PET subsystem to process the signals with little to no detrimental effect on the operation of the MR subsystem.

The PET detectors 30 include scintillation crystals or other radiation detectors that may be arranged in cassettes 60 of, for instance, six or eight detector blocks 62. The detector cassettes 60 are arranged in a ring, arc, or otherwise partly around the tubular bore region or other opening for scanning the patient. For example, each cassette 60 is positioned such that the detector blocks 62, which may be elongate to support whole body imaging and/or maximize the PET field of view, are linearly positioned or oriented along the long or main axis of the subject bore. Any number of cassettes 60 (e.g., 48, 54, 56, etc.) may be spaced around the subject bore. In one embodiment, each detector block 62 includes a crystal array (e.g., a 12×12 array of 2.5 mm crystals). The photons generated by each crystal array are captured by a number of photodiodes in each detector block 62. The photodiodes may be avalanche photodiodes (APDs). For example, nine APDs may be provided for each block 62. In other embodiments, the scintillation crystals are coupled to photomultiplier tubes. The scintillation crystals may include bismuth germanium oxide, gadolinium oxyorthosilicate, or lutetium oxyorthosilicate crystals, but other crystals may be used.

Each detector block 62 generates three output signals, two position signals and one energy signal. These signals are analog signals in APD embodiments. In other embodiments, each detector block 62 may include digital photodiodes. Each of the signals may be provided as a differential signal pair output. In an example with 56 APD-based detector cassettes 60, each having eight detector blocks 62, a total of 1,344 differential signal pairs are presented by the set of detector cassettes 60. Coaxial, twisted pair, or other cables 64 may be used to carry the analog signals from the detector blocks 62 to the DAU array 40. In one example, each cable 64 that connects one of the detector cassettes 60 with one of the DAUs 42 includes 24 signal pairs to carry the analog output signals. Alternatively or additionally, signal encoding may be used to carry the analog signals in the cables 64. Each DAU 42 may handle one or more detector cassettes 60. In this embodiment, a pair of detector cassettes 60 are coupled to a respective one of the DAUs 42. Each DAU 42 includes a corresponding number of input termination or other ports 66 to which the cassette cables 64 are attached. Each input port 66 provides an interface for each detector group of signal pairs provided by a respective one of the detector cassettes 60. The input port 66 may be configured to provide an RF tight connection and balanced interface for the differential signal pairs (e.g., 16 position and eight energy), as well as for the filtered, split power to the detector blocks 62.

Each input port 66 may be coupled to one or more circuits configured to provide front-end filtering of the cassette detector signal inputs. The circuits may include, for instance, one or more band-pass and/or low-pass filters to select the frequency range of the detector signals and block any other frequencies. For example, a pole filter may be used to block the RF excitation frequency of the MR subsystem (e.g., 123 MHz). Other filter topologies (e.g., pole or notch filters in combination with other filters) may be used. The detector signals may have a relatively wide bandwidth (e.g., 40-60 MHz). The DAU 42 includes a number of other circuits shown schematically at 67 for amplification, analog-to-digital conversion, and/or other signal processing. The circuits 67 are configured such that each PET detector event is quantized and time stamped by one of the DAUs 42.

Each DAU 42 may have a dedicated cooling interface 68 to remove the heat generated by the circuits 66. The cooling interface 68 may include a portion of the housing of the DAU 42, or include a chill plate, frame or other structure in thermal communication with the DAU housing. In one embodiment, the cooling interface 68 includes a metal platform (e.g., aluminum, copper, or any combination thereof). The metal platform or other cooling interface 68 may be coupled to the cooling system 44 (FIG. 1) or other device or system for access to, or other communication with, a cooling fluid. A variety of different coolant fluids may be used. For example, the cooling interface 68 may be water-based. Alternatively or additionally, the interface 68 may include a heat sink in thermal communication with the DAU 42. The heat sink may be configured to be exposed to forced air or other fluids.

The DAU 42 may also include one or more thermally conductive paths 70 between the thermal interface 68 and internal DAU heat sources. The thermally conductive paths 70 may include components external to the DAU housing, as well as or alternatively components within the DAU housing. The thermally conductive paths 70 may include electrically insulating gaskets or other spacers via which the DAU 42 is mounted to the cooling interface 68. The thermally conductive paths 70 may be made of thermally conductive polymer materials. In one embodiment, the thermally conductive gaskets have a thickness of about 2 mm, and are made of silicone. The materials, construction, configuration, location, and other characteristics of the thermally conductive paths 70 may vary.

The DAU 42 also includes an input termination or other port 72 for a DC power supply. The input termination 72 may include or be coupled to one or more power filters to remove any noise that may have been introduced between the RF filter plate and the DAU 42. The filtering may include one or more low-pass or notch filters. The filter(s) may be configured to block signals at the RF excitation frequency of the MR subsystem. The filter topology may vary. The filtering may be provided in addition to similar filtering provided at the filter plate 50 by a power supply filter 73.

The DAU 42 may include a number of other ports configured to provide input/output (I/O) interfaces. An I/O port 74 is configured to receive a clock signal, and an I/O port 76 is configured to support communications with the remainder of the PET subsystem. The clock signal port 74 may include a coaxial connector for receiving a sine-wave clock, which may be referenced to chassis ground (e.g., chassis ground of the PET filter plate described herein). The clock signal may be used as a system clock for the PET detector data sampling and other signal processing implemented by the DAU 42. Alternatively or additionally, a system clock may be developed from a timing signal provided via the I/O port 74. For example, the clock signal received via the I/O port 74 may be a sine or square wave, which is then used to develop a conventional square wave clock once inside the RF tight housing of the DAU 42. Transmission of the sine wave along one or more cables 77 inside the RF cabin 12 may be less of a risk to the operation of the MR subsystem than the transmission of a conventional square-wave clock. The I/O port 74 may include multiple connections to support both reception and transmission of the clock signal, which may be useful for distributing the clock signal to the entire DAU array 40 without losses or other variance.

The I/O port 76 may include an optical fiber connector to support fiber optic communication signals over a fiber optic link 78. The optical signals may include both the digitized PET detector signal data as well as control signals and other communications between the PET subsystem equipment 14 (FIG. 1) and the DAU 42. The optical fiber connector of the I/O port 76 may be configured to limit or prevent RF leaks into or out of the DAU 42.

The DAU 42 includes one or more RF shielded compartments to limit EMI from entering or exiting the DAU 42. Because the DAU 42 is located within the RF cabin, noise from the DAU 42 should be reduced to a minimum, which is challenging due to the high channel count of the PET subsystem (e.g., 1344 signal pairs coming from the PET detectors). The RF shielding of each DAU 42 achieves high levels of bi-directional attenuation at the MR frequency, for both differential and common mode signals, thereby preventing interference with the MR imaging. With sufficient attenuation, both MR and PET scans may be performed at a same time. The DAU 42 may include several components that, without shielding, may emit electromagnetic radiation at the MR frequency. These components may include front end filters and amplifiers, analog-to-digital (A/D) converters, and digital signal processing circuitry. The shielded compartments also protect these components from the gradient and RF fields of the MR subsystem. Such protection is in addition to the protection provided by a number of filters within the DAU 42 (e.g., power supply filters and clock input/output (I/O) filters).

Each DAU 42 may include a housing 80 that fully encloses its electronic components for RF tight shielding. The housing 80 may be made of one or more metals (e.g., copper) having a thickness corresponding with, for example, five skin depths at 20 kHz. The housing 80 may include any number of partitions or walls that define separate compartments for various electronic components. The partitions or walls may also have a similar thickness. Alternatively, a single compartment is formed by the housing 80.

Figure 3:
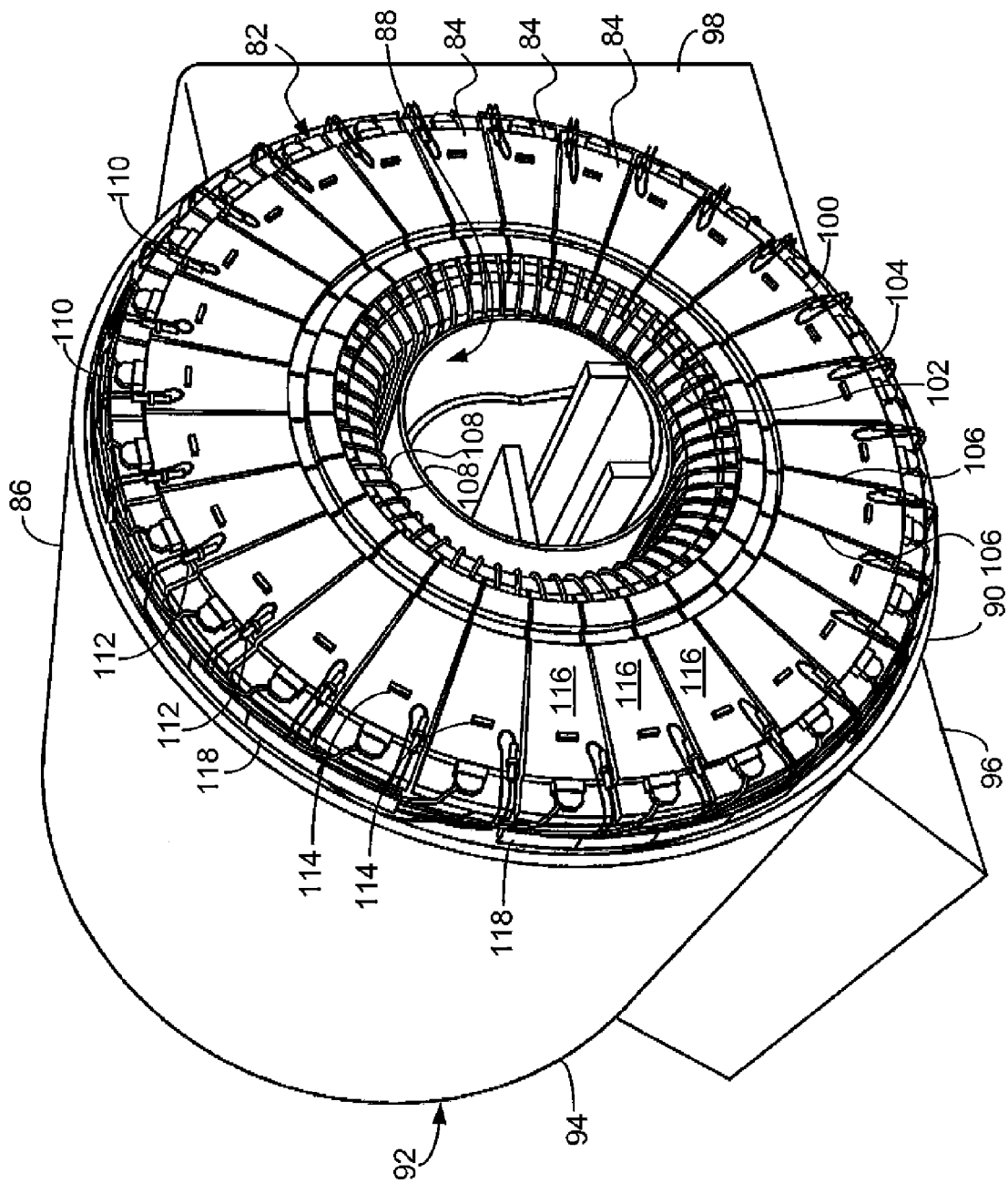
FIG. 3 is a perspective view of an integrated MR/PET scanner according to one embodiment.

FIG. 3 shows one example arrangement of an array 82 of DAUs 84 in the RF cabin. The DAU array 82 is disposed along an MR scanner 86, which may be considered a hybrid or integrated MR/PET scanner because PET detectors are disposed within a bore or opening 88 defined by a magnet of the MR scanner 86. In this example, the DAU array 82 is disposed along a planar end face 90 of an enclosure or other housing 92 of the MR scanner 86. The end face 90 may correspond with a back side of the MR scanner 86 opposite the side through which the patient table enters the MR bore 88. The enclosure 92 may include a main section 94 configured to cover the magnet 32, the gradient coils 34, the body coil 36 and other scanning components of the MR subsystem (see FIG. 1). The main section 94 has a tubular shape that matches the shape of the magnet 32 of this embodiment. The end face 90 may lie between a pair of annular rims (e.g., shaped as concentric circles). The end face 90 may have a disc-shaped or annular surface on which the array 82 is mounted or along which the array 82 is disposed. The main section 94 and other portions of the enclosure 92 may be shaped differently to match other magnet shapes. The enclosure 92 includes a base section 96 to cover a stand or other support structure, as well as an auxiliary cabinet section 98 to enclose electronics, user interface, or other auxiliary or control elements of the MR subsystem. The auxiliary cabinet section 98 may be located alongside the main section 94 and oriented along a main axis of the MR scanner 86 (or magnet).

The DAU array 82 is oriented in a plane parallel to the end face 90. Taken together as a group within that plane, the DAUs 84 form a disc- or star-shaped pattern or cluster disposed around the bore 88. Each DAU 84 is disposed along a respective radial line extending outward from the center of the bore 88. Each DAU 84 includes an RF shield housing 100 tapered to form a sector of the disc shape. The RF shield housing 100 includes an inner end 102, an outer end 104, and a pair of tapered, lateral sides 106. In this example, the lateral sides 106 are opposite sides and extend along radial or sector lines of the disc shape. The tapering leads to the inner end 102 being shorter than the outer end 104, as in a pie slice shape. Each DAU 84 may be disposed adjacent a pair of neighboring DAUs 84 with minimal spacing along the radial length of the DAU 84, allowing a large number (e.g., 28) of DAUs to fit alongside one another as a contiguous DAU array. The number of DAUs 84 in the array 82 may vary based on the number of PET detectors.

The disc- or star-shaped DAU packaging arrangement shown in FIG. 3 is configured to minimize interaction between the PET and MR subsystems. The arrangement may reduce variations in the B0 and B1 magnetic fields of the MR subsystem that might otherwise result from the noise generated by the data processing in the DAUs 84. The DAUs 84 are disposed in a symmetrical arrangement that may help reduce or minimize EMI or EMC. In this example, the symmetry is radial, or relative to the center of the bore 88, as well as axial due to the planar alignment of the DAUs 84. Both symmetrical aspects of the packaging arrangement are directed to minimizing or preventing any impact on MR image quality. PET signal integrity is also maximized via this symmetrical DAU placement, such that multiple potential interoperability issues between the MR and PET subsystems may be addressed. In alternative embodiments, the DAUs may be arranged in a half-disc or half-star configuration, or in any other configuration in which the DAUs are arranged along radial lines relative to the MR bore.

The disc- or star-shaped arrangement of the DAU array 82 does not alter the form factor of the MR scanner 86 or substantially change the dimensions of the MR scanner 86. The MR scanner 86 may be shaped and sized in accordance with strict siting conditions. The installation site of the MR scanner 86 may present restrictions on the overall length, width, and height of the unit. These restrictions may arise from the size of RF cabin doors or other installation access points. For example, the overall length of the unit (i.e., the dimension along the main axis of the bore 88) may be limited to two meters. The DAU array 82 adds little to that length, because each DAU 84 is oriented along the same, upright plane adjacent the MR scanner 86 and because each DAU 84 has a flattened profile. The lateral dimensions of each housing 100 exceed the height (or thickness relative to the main axis of the bore 88) of the housing 100, where the lateral dimensions correspond with the dimensions aligned with the upright plane along which each DAU 84 is disposed. The DAUs 84 also may not extend radially beyond the end face 90 of the MR scanner 86. The RF shield housing 100 of each DAU 84 may have a radial length that corresponds roughly with the radial extent of the annular surface of the end face 90. The DAUs 84 avoid blocking the opening of the bore 88 by not extending beyond an inner rim of the end face 90, and allow the MR scanner 86 to remain mounted on a standard support structure in the base section 96 by not extending beyond an outer rim of the end face 90.

In this arrangement, each DAU 84 in the array 82 services a pair of PET detector (e.g., avalanche photo diode) cassettes located within the MR bore 88 in front of the gradient coil and behind the body coil RF screen (FIG. 1). A pair of PET detector cables 108 terminate at a connector located at the inner end 102 of the DAU 84. The disc- or star-shaped arrangement minimizes the length of each cable 108, insofar as the inner end 102 is located adjacent the edge of the bore 88. The minimal length of the cables 108, in turn, minimizes the distortion of the analog signals developed by the avalanche photodiodes before the analog signals are digitized in the DAUs 84. The DAU packaging arrangement also allows each cable 108 to have the same length. The equal lengths and evenly spaced radial positioning of the cables 108 provide additional radial symmetry to minimize EMI and EMC.

Another connector 110 is located at the outer end 104 of the DAU 84 for the termination of a dedicated power cable for each DAU 84. In this example, separate connectors are provided for the clock, control, and data signals, although a common connector may be used. A connector 112 is located at the outer end 104 for the clock signal, and a connector 114 is located on a front face 116 of the housing 100 for the fiber optic link carrying the incoming control information and outgoing PET data. The connector 114 may include a slotted block of, for example, metal, configured as a socket or other opening to receive ends of the fiber optic link All of the above-described connections may be configured to present radially symmetrical interconnect cabling leading to and from the DAUs 84. The symmetry of the interconnect cabling is relative to the MR magnet bore 88. Such symmetry minimizes or reduces EMI and EMC between the MR and PET subsystems. EMI and EMC may be further reduced by routing the interconnect cabling through one or more cable guides 118 disposed along the outer rim of the array 82, which, in this case, corresponds with the outer rim of the end face 90 of the enclosure 86. Each cable guide 118 may be configured as an elongate bracket having a curvature that matches the curvature of the outer rim. In this example, the cable guide 118 may be an L-bracket, but a variety of other configurations may be used.

Performance of the PET subsystem is improved by locating the DAUs 84 near the PET block detectors (FIGS. 1 and 2). The number of DAUs 84 may vary from the example shown. Spreading the DAUs 84 around the radial extent of the MR housing may also provide advantages in keeping the cabling, RF and thermal densities to moderate levels. The packaging arrangement is thus scalable. The system is also scalable because of the modularity of the DAU array 82. Manufacturability and serviceability may also be enhanced by the modularity of the DAU array 82. For example, the DAU array 82 may be partitioned to diagnose a problem.

Figure 4:
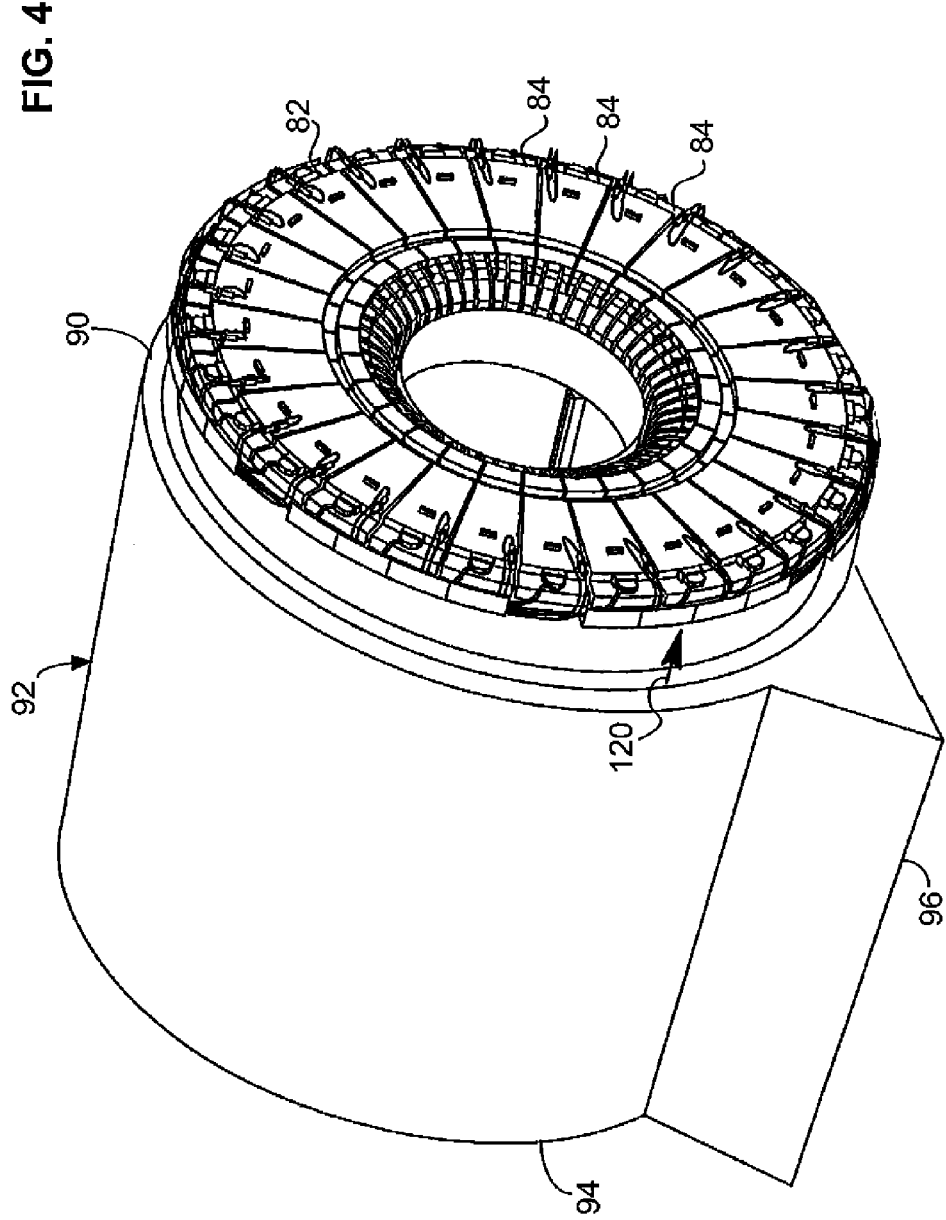
FIG. 4 is a perspective view of a PET subsystem of the integrated MR/PET scanner of FIG. 3 according to one embodiment.

FIG. 4 shows how the location of the DAU array 82 in the RF cabin may be optimized or adjusted relative to the MR scanner 86. The location of the DAU array 82 may be adjusted to optimize a spacing between the DAU array 82 and the MR subsystem. Adjusting that spacing may allow levels of EMI or EMC to be reduced, which may be useful in connection with MR subsystems having high field strengths or fringe fields. For instance, the fringe field may vary between MR subsystems based on differences in the type, strength, or depth (i.e., axial length) of MR magnet or bore. The DAU array 82 may be movable in the axial direction (i.e., the direction of the main axis of the MR magnet) to introduce a gap 120 between the end face 90 of the enclosure 92 and a support framework or other structure on which the DAUs 84 are mounted.

The support framework may include a base (not shown) on which the array 82 rests. The construction, configuration and other characteristics of the base and the support framework may vary considerably. The base may be used to position the array 82 at a desired distance from the MR magnet and/or other components of the MR subsystem.

The disc- or star-shaped arrangement of the DAU array 82 and the mounting of the array 82 on a base allows the gap 120 to be optimized. The size of the gap 120 may be adjusted to address differences in the depth of the magnet bore. Examples of gap sizes include embodiments in which the gap size is less than or roughly equal to the axial thickness (or height) of each DAU 84, e.g., about 4 inches or less, and embodiments in which the gap is longer than the axial thickness of the DAU 84, e.g., from about 8 to about 10 inches. The gap size may range from zero to any desired spacing.

The relative positioning of the DAU array 82 relative to the MR scanner 86 (e.g., away from the scanner 86 in the axial direction) may be useful to mitigate Lorenz forces and/or B0/B1 homogeneity degradation. The time-varying magnetic fields from the MR gradients induce currents in any metal structures of the DAU array 82 (e.g., each DAU housing), causing the metal structures to vibrate, which, in turn, creates magnetic fields that may oppose or otherwise degrade the MR fields. Increasing the size of the gap reduces the Lorenz forces to reduce such degradation. In alternative embodiments, the DAU array 82 is fixed to the MR scanner 86 without an assembly to adjust any gap.

Figure 5:
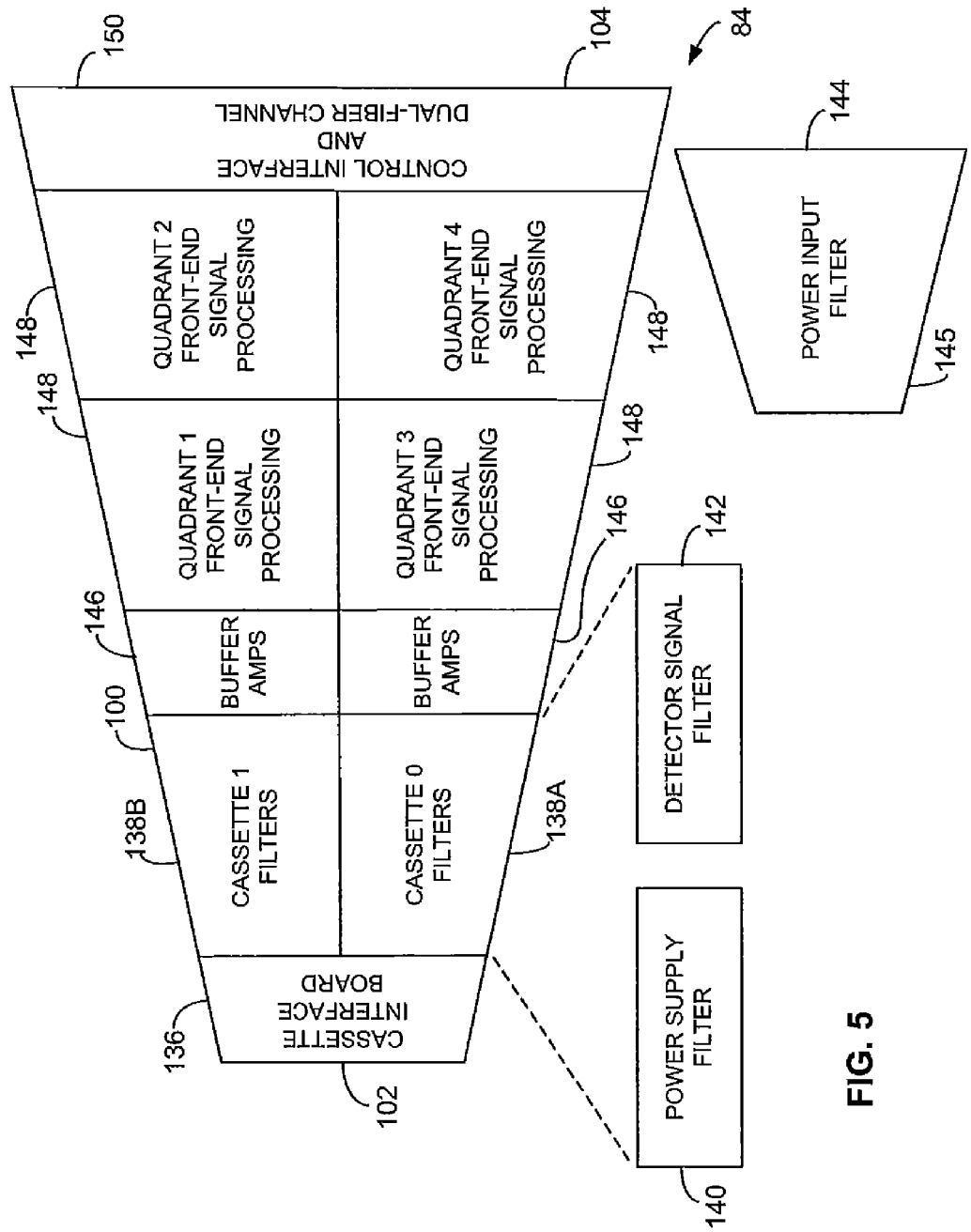
FIG. 5 is a block diagram of a data acquisition unit of the PET subsystem of FIG. 4 according to one embodiment.

FIG. 5 shows a schematic view of one of the DAUs 84 in an example embodiment having the tapered housing 100, but non-tapered housings may be used. Near the inner end 102, the DAU 84 includes an interface board 136 to support the pair of connections with the PET detector cassette cabling. The interface board 136 receives the cassette cabling and may provide an interconnect to both the detector signal and the power filters. The interface board 136 may be passive. The interface board 136 is part of an analog section of the DAU 84 that also includes a number of filters to remove the noise generated by the RF excitations of the MR subsystem (e.g., 123 MHz). The interface board 136 and other components of the analog section of the DAU 84 may be disposed in one of multiple, separate compartments of the housing 100. The filters may be arranged in a pair of cassette filter sets 138A, 138B, one for each of the detector cassettes serviced by the DAU 84. Each set 138A, 138B may include one or more power supply output filters 140 and one or more detector signal filters 142. The detector signal filters 142 generally block the RF excitation frequencies from reaching the downstream components in the DAU 84, such as the analog-to-digital converters. The detector signal filters 142 also prevent any noise from the DAU 84 at those frequencies from interfering with the operation of the MR subsystem. The power supply output filters 140 provide similar functionality with respect to the DC power delivered to the PET detectors 30 (FIG. 1). Power delivered to the DAU 84 is filtered by a power input filter 144, which may be disposed on a dedicated board 145. The power input filter 144 may be disposed in a discrete housing adjacent to the housing 100, or be disposed in a dedicated compartment of the housing 100. The analog section of the DAU 84 also includes a pair of buffer amplifiers 146, which may be configured to drive further amplifiers (e.g., flash amplifiers) in the digital section of the DAU 84. Further filtering at the MR RF frequency may occur at the interface between the analog and digital sections of the DAU 84.

The digital section of the DAU 84 may include a number of discrete units for processing the signals from respective sets of PET detector blocks separately. In this example, the digital section includes signal processing quadrants 148, each of which may handle a number of detector blocks (e.g., four detector blocks). Each signal processing quadrant 148 may include analog-to-digital converter circuitry, such as feedback amplifiers and other devices, for sampling or otherwise digitizing the analog detector signals. The digital section of the DAU 84 also includes an I/O interface 150 at the outer end 104 of the DAU 84, which may be configured for dual-fiber optical communications with other components of the PET subsystem. The optical communications may include reception of control signals and transmission of digital data representative of the PET detector signals. The digital section of the DAU 84 may be enclosed in one of the separate compartments of the DAU housing 100.

Figure 6:
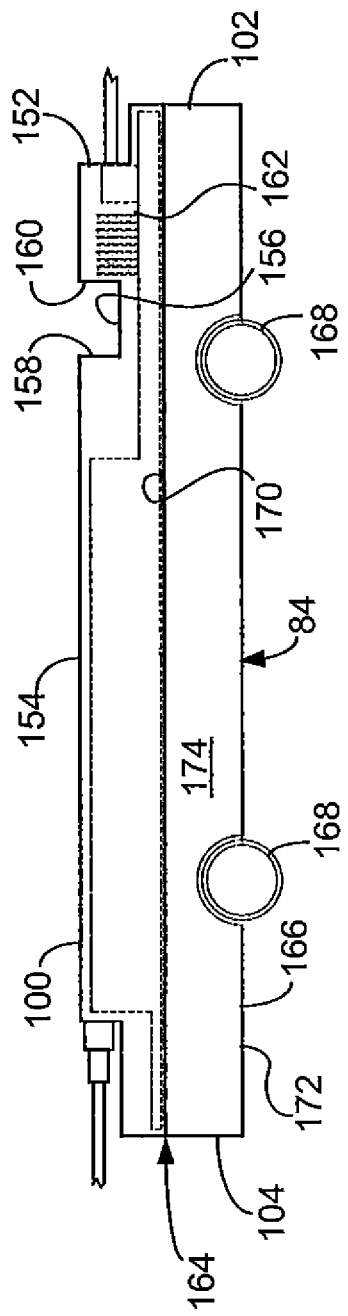
FIG. 6 is a side, elevation view of the PET data acquisition unit of the PET subsystem of FIG. 4 according to one embodiment.

Each compartment of the DAU housing 100 may be RF shielded from the other compartments via a wall or other divider. The walls or dividers may be aligned with one or more grounding traces on a circuit board of the DAU 84 to isolate the compartments from one another. The compartments need not correspond with the lines shown in FIG. 5. The walls or dividers defining the compartments may be constructed in the same manner as the external walls of the housing 100. One or more of the walls or dividers may, in fact, correspond with external walls of the housing 100. As shown in the example of FIG. 6, the housing 100 includes a compartment 152 disposed near the inner end 102. The compartment 152 is separated from a main compartment 154 of the housing 100 via a notch 156 defined by a pair of walls 158, 160. In this example, the compartment 152 encloses circuitry 162 disposed on the cassette interface board 136. The components of the DAU 84 disposed in separate compartments may vary, including, for example, the location of any external walls of the housing 100 that act as dividers.

FIG. 6 also shows one example of a cooling interface 164 for thermal management of each DAU 84. The cooling interface 164 includes an area in which the housing 100 is adjacent to a thermally conductive structure 166. Cooling pipes or other conduits 168 are in thermal communication with the structure 166, which, in turn, is in communication with the housing 100 via the interface 164. Heat generated by the circuitry in the DAU 84 is dissipated via the fluid passing through the cooling pipes 168. Each cooling pipe 168 may run through or adjacent to each of the DAU housings 100. In some embodiments, including those having the tapered DAU housings forming the disc-shaped arrangement, the cooling pipes 168 may be shaped and disposed as concentric rings.

In one embodiment, the thermally conductive structure 166 includes a metal platform on which the housing 100 rests. For example, the metal platform may be made of aluminum and copper. The platform includes a flat, top side 170 that defines the interface 164 and a bottom side 172 opposite the top side 170. The platform includes a number of sidewalls 174 between the top and bottom sides 170, 172. The bottom side 172 may be open or partially open to allow air cooling of the interface 164. Forced air cooling may be provided as an alternative, or in addition, to the cooling provided by the pipes 168.

Figure 7:
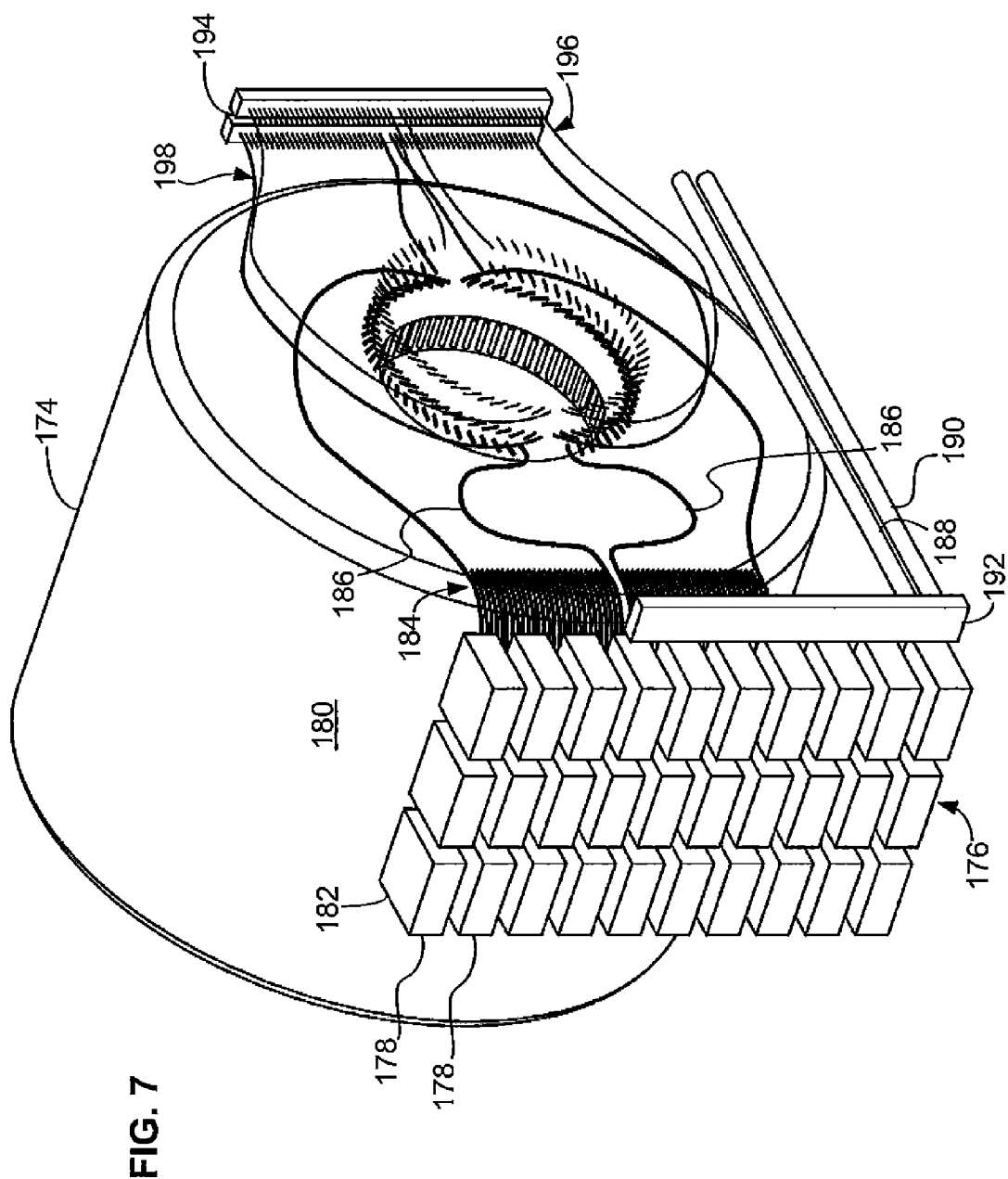
FIG. 7 is a perspective view of an integrated MR/PET scanner according to another embodiment.

FIG. 7 shows an alternative integrated MR/PET scanner 174 that provides a packaging arrangement for an array 176 of a DAUs 178 within the RF cabin. The DAU array 176 is located along a side 180 of a housing or enclosure 182 of the scanner 174. The location on the side 180 differs from the location along an end face of the above-described disc- or star-shaped DAU arrangement. For instance, the end face has the MR bore or patient opening. In this embodiment, the DAU array 176 may be located along one or more of the sides or surfaces of the housing 182 not having a magnet bore or opening. The side 180 corresponds with a lateral or longitudinal surface of the housing 182 disposed along an axial length of the MR scanner. The side 180 is disposed between the faces having a magnet bore or other opening. In this example, the side 180 is a curved surface. The curvature may match that of the MR magnet enclosed by the housing 182. However, the housing 182 need not have a shape that corresponds with the MR magnet of the scanner 174.

The lateral location of the DAU array 176 along the side 180 may be useful from both a static magnetic field magnitude standpoint (e.g., the B0 field) and a dynamic, or time varying, field standpoint (e.g., the gradient and B1 fields). The DAU array 176 may be subjected to diminished fringe field strengths in the lateral region along the side 180. The extent to which degradation of the B0 and B1 fields may occur is reduced. Also, less noise at the MR frequency (e.g., 123 MHz) may be introduced into the I/O signals and power cabling for each DAU 178 with the array 176 at the lateral side location.

The DAU array 176 may be distributed among multiple side locations. The DAU array 176 need not be located along a single lateral side. For example, one-half of the DAUs 178 may be disposed along one lateral side, while the other half of the DAUs 178 are disposed on the opposite lateral side. The axial positioning of the two sets of DAUs 178 may be matched to provide axial symmetry relative to the MR magnet and other subsystem components.

Whether disposed on one or more lateral sides, the DAUs 178 of the array 176 may be disposed in a rack pattern or arrangement that may support symmetries relative to the MR subsystem or MR fields. The DAUs 178 of the array 176 are stacked in one or more columns or other groupings. In this example, the DAUs 178 are stacked in a rack pattern having three columns disposed in a row oriented in parallel with the main axis of the MR magnet. The columns may have an equal height (e.g., an equal number of DAUs 178) to provide one or more degrees of symmetry relative to the MR fields. Further symmetries are provided by equal spacing between the columns and equal spacing between individual DAUs 178 in each column. The rack pattern need not dispose the DAUs 178 in vertical stacks. For example, the DAUs 178 may be stacked or mounted in a non-vertical manner to, for instance, track the curvature of the housing 182. The number of DAUs 178 in each column may vary such that columns may have an unequal number of DAUs 178.

The DAUs 178 may be supported by shelves, mounting brackets, or other structures projecting from a back panel or other riser. The DAUs 178 may be grounded to the MR magnet in one or more groups. The support structure and collective grounding notwithstanding, the DAUs 178 within the rack-mounting arrangement may be galvanically isolated from one another as described further below. The support structures may include, define, or support a respective cooling interface for each DAU 178. One example cooling interface uses the spacing between the DAUs 178 as a flow path for forced air or other cooling fluid(s).

Each DAU 178 need not have a box-shaped housing 182 as shown in FIG. 7. The lateral side location of the DAU array 176 is not limited to any housing shape, profile, or form factor. The DAUs 178 need not be stacked in the orientation shown. For example, each DAU 178 may be rotated to a more vertical or upright orientation with each DAU 178 disposed on an end adjacent to an end of a neighboring DAU 178. In such an orientation, the larger faces of all of the DAU housings 182 are aligned in a pair of planes.

As with the above-described embodiments, the DAU array 176 presents a modular architecture for the processing of the PET detector signals. Each DAU 178 may receive signals from one or more PET detectors. In this example, each DAU 178 may service two detector cassettes. The DAU array 176 may thus support a large number (e.g., 56 or 60) of detector cassettes.

The rack pattern of the DAU array 176 may also provide a symmetrical arrangement of PET detector cabling. Cables 184 extend from the DAUs 178 to the bore or opening as shown schematically in FIG. 7. In this example, an upper half of the cables 184 may connect to an upper half of the PET detectors, while a lower half of the cables 184 may connect to a lower half of the PET detectors. Such interconnect cabling may be symmetrical about a horizontal line segment passing through the center of the bore. Further symmetry about the MR bore (or the line segment passing through the bore) may be achieved by equalizing the lengths of the cables 184. For those cables 178 that enter the bore nearest to the DAU rack, the cables 184 may be deflected upward (or downward) along a portion 186 to introduce extra length, and may run to the DAUs 178 in the column farthest away from the bore. Even with the added length, the overall length of each cable 184 is still relatively moderate, and short in comparison with systems in which the analog detector signals are carried outside of the RF cabin. These symmetries may be useful in connection with both closed and open MR subsystems.

Heat generated by the DAU array 176 may be removed by a cooling interface provided with water or other fluid transported via pipes 188, 190, which terminate at a manifold 192. Tubing may then carry the fluid along paths in thermal communication with the DAUs 178. One example of such tubing is shown in connection with another manifold 194 that provides fluid to cool the PET detectors in the MR bore. The manifold 194 supports a set of tubes 196 to deliver chilled fluid to the PET detectors and a set of tubes 198 that return the fluid after exposure to the heat generated by the PET detectors.

The disclosed systems may include a power distribution system to support the location of the PET subsystem electronics of the DAUs in the RF cabin. The power distribution system may include the filter plate 50 and the modular power supply system 52 shown in FIG. 1. Further details regarding examples of these power distribution components are presented in connection with FIGS. 8 and 9.

The power distribution system may be configured to supply power to the PET subsystem components in the RF cabin while keeping the power spectral density of the PET electronics (e.g., the above-described digital sampling and processing circuitry) controlled and out of the MR receiver frequency bands (e.g., 123.212 MHz+/−500 KHz for 3 T MR subsystems). This aspect of the power distribution system may be challenging in view of the length of the power cabling (e.g., up to about 15 meters), and in view of the current magnitudes involved (e.g., a total of about 850 A to the DAUs and the PET detectors). In one example, the power distribution system supplies approximately 4 kW of power to the PET subsystem components in the RF cabin. The power distribution system also distributes multiple classes of power to each DAU and detector cassette in a way that minimizes the EMI/EMC susceptibility of the PET subsystem to the MR gradient switch-mode noise, gradient fields, and RF bursts.

The power distribution system may include separate power sources for the MR subsystem. For example, a Verio 3 T gradient amplifier may be used to supply up to 4 kV at 1000 A peak to each of three gradient coils. The MR Body coil may be driven by an RF power amplifier capable of delivering 35 KW of power. Without more, EMI from these MR power sources can be coupled into the PET power cables.

The power distribution system may support PET subsystem digital sampling and digital signal processing on the large scales described above within the MR RF cabin via a number of isolated, floating, modular power supplies. Each power supply may drive a respective DAU though an individual filter module interconnected with shielded twisted pair cabling such that power is distributed in a star configuration to the DAU/PET detector load.

Figure 8:
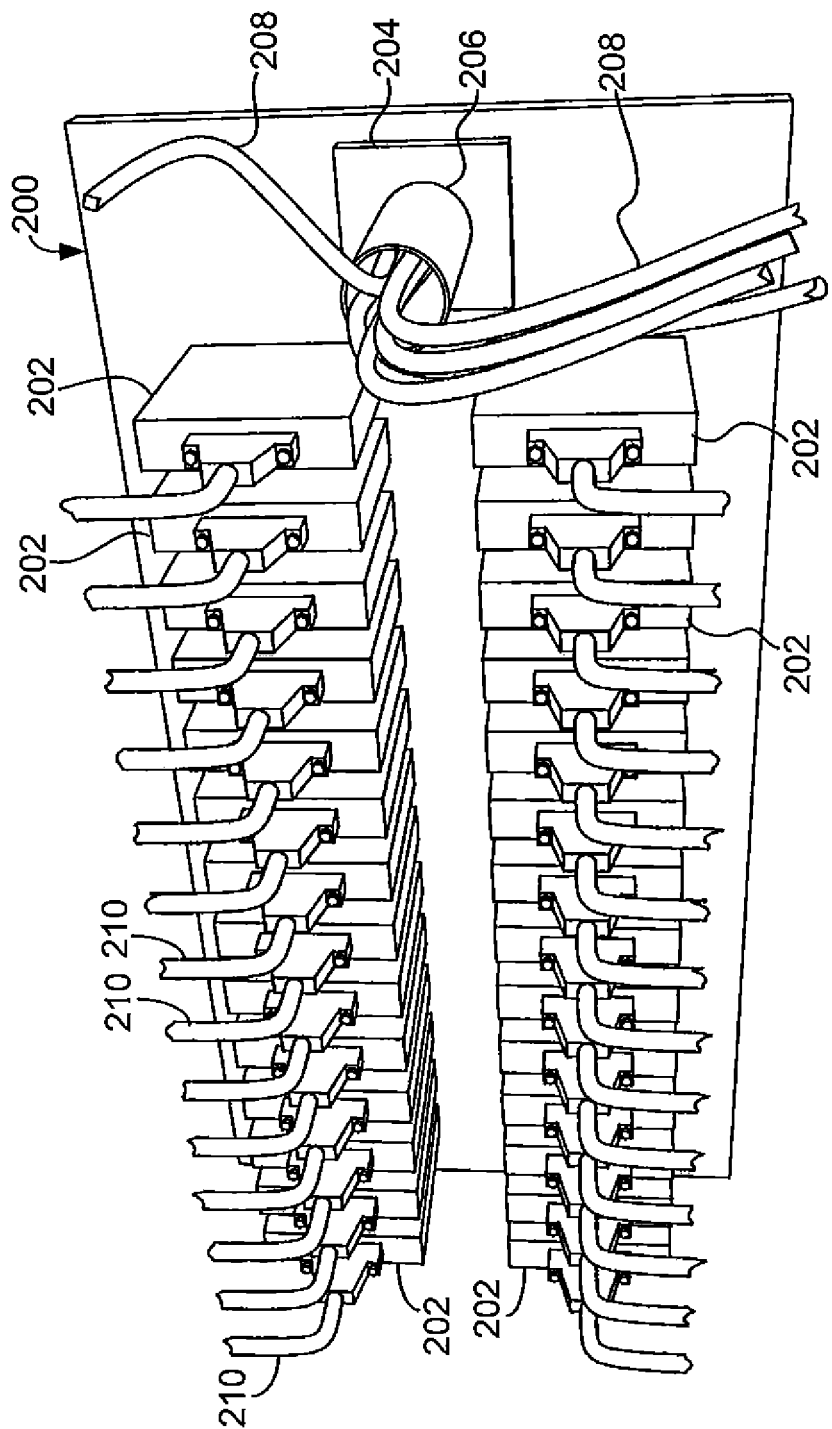
FIG. 8 is a perspective view of a filter panel at an RF cabin interface according to one embodiment of the disclosed integrated MR/PET imaging systems.

FIG. 8 shows one example of a filter plate 200 of the power distribution system. The filter plate 200 may be mounted to define RF tight access to the RF cabin. The filter plate 200 includes a respective power filter 202 for each DAU in the DAU array. This modular approach may be extended to the power supplies outside of the RF cabin, as described below. Each power filter 200 may thus be associated with a respective power supply module/DAU pair. Each power filter 200 may be configured to remove or block any frequencies that may disturb the MR subsystem, including those in the MR receiver bands. The filter plate 200 may also include a port 204 for the fiber optic communications between the DAUs and the PET subsystem equipment outside of the RF cabin. The port 204 may include a metal tube 206 or other conductive structure dimensioned and otherwise configured to act as a waveguide filter that blocks frequencies in the RF receiver bands from entering the RF cabin. The aspect ratio of the tube 206 may be selected such that RF noise at those frequencies cannot pass through the tube 206. For example, the tube 206 may have a diameter of in a range from about 2.5 to about 3.0 inches and a length in a range from about 12 inches to about 16 inches. The diameter is selected to provide ample room for a number of fiber optic cables 208, each of which may constitute a bundle of fiber optic links Each link may have a dual fiber configuration to support both input and output communications for a respective DAU.

The filter plate 200 may also include one or more additional RF tight interfaces or access ports for a system ground reference (including a ground reference mounting location) and one or more clock signal lines. In one embodiment, a single clock signal (e.g., a sine wave) is provided via the filter plate 200 to a splitter (e.g., 1:30) in the RF cabin. The filter plate 200 may alternatively support the transmission of multiple clock lines leading from a splitter or other circuitry located outside of the RF cabin.

In this embodiment, a respective power cable 210 runs from each power filter 202 to a corresponding one of the DAUs in the array. In an alternative embodiment, a single power cable may support more than one DAU by way of a power distribution network within the RF cabin. Each power cable 210 also supports the pair or other number of PET detector cassettes associated with the DAU. The respective power cables 210 distribute power in a star configuration. As a result of this and other aspects of the power distribution system (e.g., modularity), each DAU is galvanically isolated from the other DAUs. The power cable 210 and other cabling in the power distribution system may be externally shielded and tied to the chassis ground of the filter plate 200. Each power cable 210 may include internal power cable conductors such as twisted pair for single-ended power, twisted triplet for split rail power, and coax for high voltage power.

Figure 9:
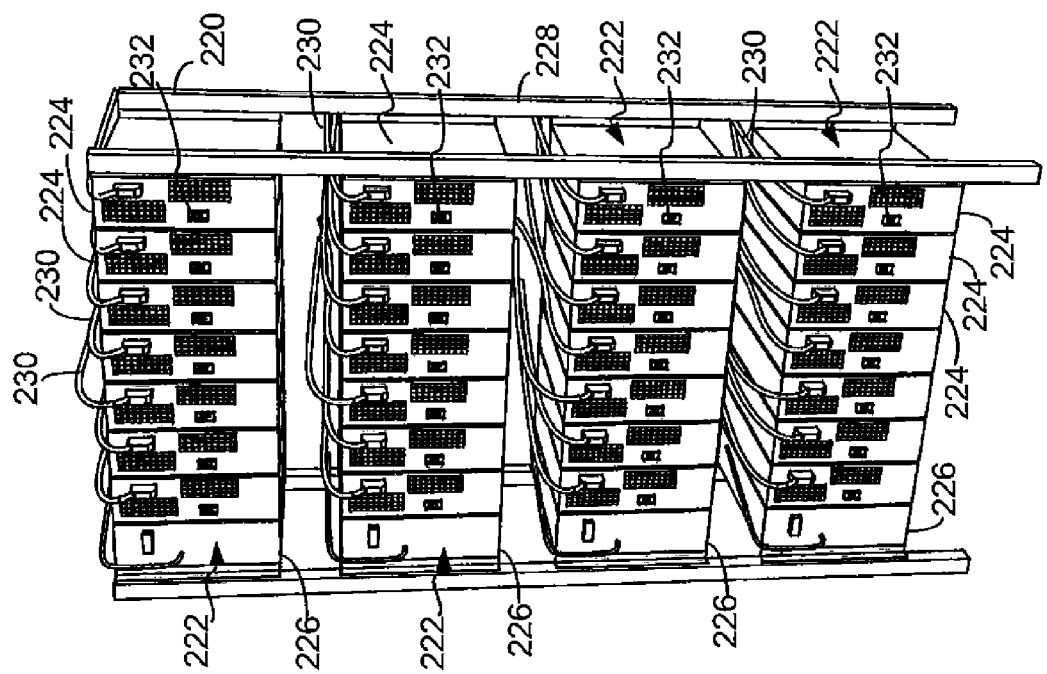
FIG. 9 is a perspective view of a modular power supply and communications rack according to one embodiment of the disclosed integrated MR/PET imaging systems.

FIG. 9 shows examples of a power supply rack 220 of the power distribution system. The power supply rack 220 is located outside of the RF cabin (i.e., on the other side of the filter plate). The power supply rack 220 supports a modular approach to providing power to the DAU array and PET detectors. The power supply rack 220 includes a number of PET power supply subsystem (PPSS) assemblies 222. This example has four such subsystem assemblies 222. Each subsystem assembly 222 may have a number of discrete power supply modules (PSM) 224 driven by a power supply hub (PSH) 226. The modules 224 and hubs 226 are mounted or housed in a main chassis 228, which may have mounting brackets or other interface into which the modules 224 and the hubs 226 may be plugged. The entire PET subsystem within the RF cabin (including, e.g., 28 DAUs) may be supported by four or other number of PPSS assemblies 222. The modular and pluggable nature of the system allows the system to be adjusted or scaled to accommodate different PET subsystems having different DAU arrangements.

Each module (PSM) 224 may run off of AC line voltage (230V) supplied by the PSH 226. Each hub (PSH) 226 filters the AC line voltage (230V) and distributes the filtered line voltage to the PSMs 224. Each PSM 224 may generate isolated low-voltage power and high-voltage power. The low voltage power may be directed to supporting the operation of the DAU and the PET detectors, while the high voltage power may be directed to supporting the operation of the PET detectors. Each PSM 224 may deliver such power outputs through a common-mode power output filter. Each power supply module may include switch-mode power supplies phase-locked to a PET system clock and/or MR time base. The common-mode power output filters of each PSM 224 may help address the considerable common-mode noise that may be generated in a switch-mode power supply scheme. Alternatively, each power supply module includes one or more linear power supplies.

Each hub (PSH) 226 may include a communications multiplexer using, for example, the I²C communication protocol, configured to monitor and control each PSM 224 in the subsystem 222. Other communication protocols may be used. Each PSM 224 has a companion power filter 202 (FIG. 8) located on the PET filter plate 200 (FIG. 8) mounted on the RF cabin. Respective cabling 230 may couple the filters 202 and the PSMs 224. Each PSH 226 may also provide input line filtering, and include an input circuit breaker.

Each PSM 224 may have a circuit breaker 232 or other switch to control the operation of the PSM 224. The circuit breaker 232 may cut power to the entire PSM 224 or otherwise disconnect, shut down, or deactivate the PSM 224. Deactivating or disconnecting one of the PSMs 224 may be useful in connection with diagnosing an operational problem (e.g., for manual EMI/EMC shielding troubleshooting). For example, if an RF leak is detected, any number or set of the PSMs 224 may be shut off to determine which one(s) of the PSMs 224 may be responsible for the leak. The modularity of the PSMs 224 and other components of the power supply distribution system provides a serviceable system. Each PSM 224, power filter 202 (FIG. 8), and DAU are scaled up as a group, with each group isolated from each other group.

The PSMs 224 and the PSHs 226 may be enclosed in EMI-shielded housings. Each housing may have any number of vents for air cooling.

Figure 10A:
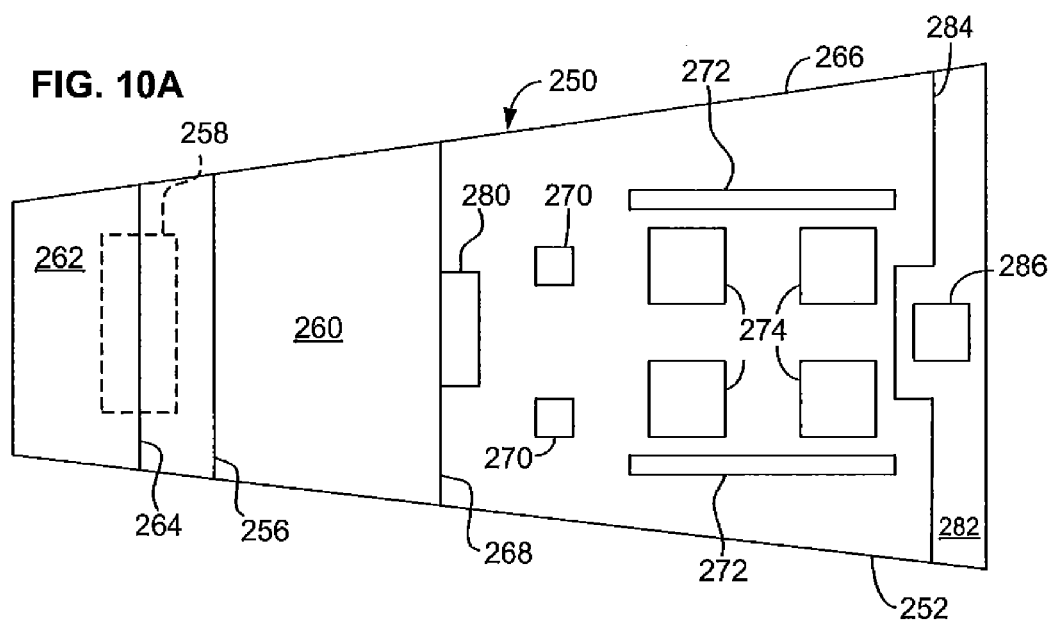
FIGS. 10A and 10B are schematic top and bottom views of a printed circuit board (PCB) assembly of a PET data acquisition unit according to one embodiment.
Figure 10B:
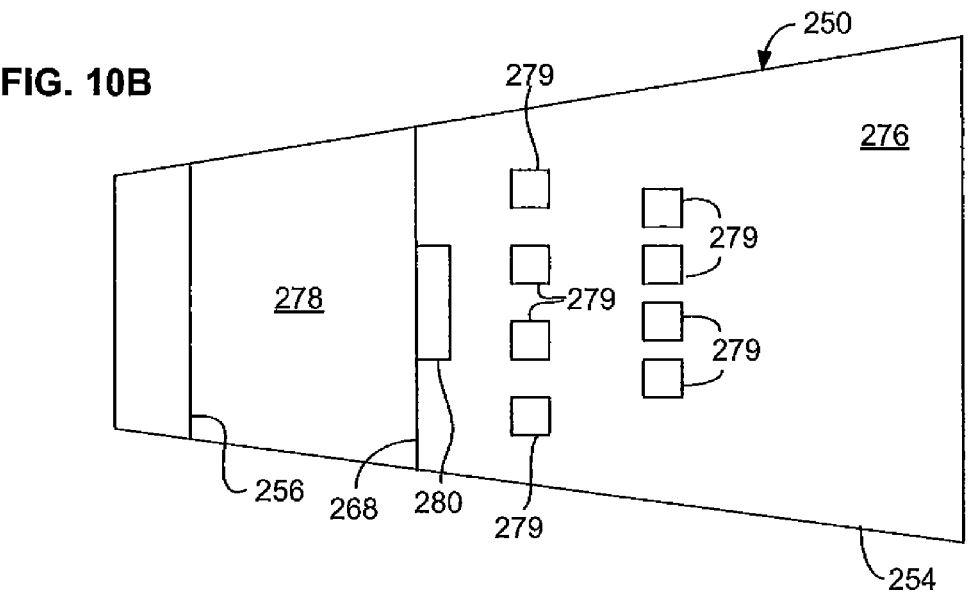

FIGS. 10A and 10B schematically depict an example printed circuit board (PCB) assembly 250 in which partitioning is used to minimize EMI emissions from, and susceptibility in, the DAUs. Geographic partitioning of the PCB assembly 250 may lead to low EMI emissions despite data processing implemented by each DAU. In one example, a number of DAUs (e.g., 28 DAUs) process 1.3 Terra bits of data per second from 1,344 differential signals received from the PET detectors coupled to the DAUs (i.e., a total of 2,688 individual signals). Emissions are reduced in this example despite the large-scale sampling and digitization of those differential signals with 1,344 twelve-bit A/D converters and subsequent processing with a corresponding number of high-density field programmable gate arrays (e.g., 140 FPGAs). Emissions are also reduced via a configuration of the PCB assembly 250 that integrates EMI shielding into the circuit layouts of each DAU and localizes power distribution and management.

The PCB assembly 250 includes a number of PCB layers arranged in a stack. A top PCB layer 252 is shown in FIG. 10A, while a bottom PCB layer 254 is shown in FIG. 10B. Any number of PCB layers may be disposed between the top and bottom PCB layers 252, 254 to route signals in support of various DAU functions. The integrated shielding and geographic partitioning of the PCB assembly 250 may be provided within specific layers and/or between layers. In this example, shielding and partitioning is provided within a given plane of the PCB layers by a number of ground partitions. Similar partitioning may be provided in more than one plane. Further shielding and partitioning is provided vertically (e.g., between or across the stack) in the PCB structure via the PCB layers themselves. For example, signal transmission may be confined to interconnects formed in one or more PCB layers near the top layer 252 (e.g., the top eight layers of the stack). RF currents may thus be confined to small regions or volumes. With no RF signals flowing beneath the upper subset of the PCB layers, shielding is provided by the remaining PCB layers lying beneath the uppermost layers (such as those near the bottom layer 254). The lower subset of the PCB layers may be directed to power distribution and regulation, as described further below. Other distribution of functions amongst the layers may be provided.

A number of ground partitions geographically separate respective adjacent circuit regions on the top PCB layer 252 and/or other PCB layers of the assembly 250. One or more of the ground partitions may be coupled to chassis ground of the DAU by, for example, a seam, wall, or other component of the DAU housing as described herein. The ground partitions may be used to separate analog circuits from mixed signal circuits, and/or to separate mixed signal circuits from digital circuits.

In the example of FIG. 10A, a ground partition 256 separates a detector filter interface 258 from an input buffer amplifier region 260. The detector filter interface 258 may be directed to filtering the incoming PET detector signals, the power supplies for the PET detectors, and the i²C communications bus. The detector filter interface 258 may include a number of circuit boards dedicated to each of these filter functions. The filter boards may be mounted transversely to the top PCB layer 252 of the PCB assembly 252 and a PET detector interface board 262, which may be independent from the PCB assembly 250. Each filter board may thus straddle a gap 264 or other divider between the PCB assembly 252 and the interface board 262. The filter boards may be disposed in parallel to one another. Alternatively, the components on the interface board 262 are disposed on an extension of the PCB assembly 250. Those components may then be separated from the detector filter interface 262 by a ground partition along the line formed by the gap 264. The detector interface board 262 may thus be integrally formed with the top PCB layer 252 as an extension thereof. The PCB layers of the stack may thus be sized differently from one another.

The detector interface board 262 may be configured to couple multiple PET detector cables to the PCB assembly 250 via a number of detector signal filters and power supply filters in the detector filter interface 258. The detector interface board 262 may couple the PET detectors to the multiple analog signal filters in the detector filter interface 258. In one example, the detector interface board 262 couples a pair of PET detector cables with six eight-channel analog signal filters. The detector interface board 262 may also be configured to couple the output power and i²C filters of the detector filter interface 258. Solder mask along the perimeters of the upper and lower sides of the detector interface board 262 may be removed to reveal a ground partition for coupling to the DAU housing. Further details regarding the coupling to the DAU housing via one or more EMI gaskets are set forth below. In one example, the solder mask may be removed via an exposure of 100 mils and a finish of emersion silver or gold flash.

The analog circuitry in the input buffer amplifier region 260 may be separated from the mixed signal circuitry of a signal processing region 266 by a ground partition 268. The mixed signal circuitry includes circuitry for analog-to-digital conversion and other PET data processing. For example, the mixed signal processing region 266 may include a number of analog-to-digital (A/D) converters 270 for sampling the position signals received from the PET detectors. Further A/D converters 270 may be provided in the mixed signal processing region 266 to sample the energy signals received from the PET detectors. The energy A/D converters in this example are mounted in a pair of geographically partitioned regions 272 within the mixed signal processing region 266. The regions 272 are defined by respective ground partitions that may be formed and configured in a manner similar to the above-referenced ground partitions. One or more other components may be separated from other mixed signal processing circuitry by ground or other partitions within the mixed signal processing region 266. For example, the region 266 may include a number of areas 274 where solder mask is removed to expose the underlying ground plane (e.g., silver) to couple to one or more elements of the DAU housing, such as one or more walls or seams. The areas 274 may thus define local shielding for respective separated regions or compartments for a corresponding number of circuits, e.g., field programmable gate arrays (FPGAs).

The ground partitions 274 and, thus, the corresponding FPGAs, may be arranged in separate quadrants or other sections of the mixed signal processing region 266 dedicated to specific PET detector blocks (or other groups of PET detector signals). Each quadrant or section may process the PET detector signals from a respective number of PET detector blocks (e.g., four PET detector blocks). The mixed signal processing region 266 may thus be arranged in a PET detector block-specific scheme, with the components dedicated to processing PET detector signals from a certain block (or blocks) located within a respective section of the region 266. This layout of the PET signal processing into quadrants or other sections on the PCB assembly 250 may minimize signal travel during the PET signal processing.

This quadrant—or other PET detector block-based layout may be extended to other circuit regions (e.g., analog or digital regions) and other PCB layers of the assembly 250, as described below. For example, the bottom PCB layer 254 (FIG. 10B) may include a region 276 directed to regulating power for the mixed signal processing components of the top PCB layer 252. The mixed signal processing region 276 may be separated from an analog region 278 of the bottom PCB layer 254 by the ground partition 268. In this example, the mixed signal processing region 276 includes a number of local linear regulators 279. Each linear regulator 279 may be dedicated to a respective quadrant or other section of the mixed signal processing region 266. The positioning of the linear regulators 279 on the bottom PCB layer 254 may not align with the positioning of the quadrant or other section of the mixed signal processing region 276. Each linear regulator 279, while local to a respective quadrant or section, need not lie directly under the devices or components that the regulator 279 powers in that quadrant or section. An offset in the positioning of the linear regulators 279 relative to the devices in the corresponding quadrant or other section may help with thermal management. Alternatively, the positions are not offset.

Power may enter the PCB assembly 250 via a connection or other interface disposed within a ground partition 280. A power input filter board (FIG. 5) may be coupled to the PCB assembly 250 via the interface. The ground partition 280 and, thus, the interface for the power input may be positioned between the input buffer amplifier region 260 and the mixed signal processing region 266 on the top PCB layer 252, and between the circuit regions 276 and 278 on the bottom PCB layer 254. A number of vias carry the input power from the top PCB layer 252 throughout the thickness of the PCB assembly 250 to the bottom PCB layer 254. The geographic partitioning of the power input extends throughout the PCB assembly 250, as the ground partitions 268 and 280 also reach the bottom PCB layer 254 as shown in FIG. 10B.

The top PCB layer 252 also includes a control interface region 282 separated from the mixed signal processing region 266 by a ground partition 284. The control interface region 282 may include an FPGA 286 and other digital components for data transfer and other processing of the digitized representations of the PET detector signals. The control interface FPGA 286 may be geographically separated from the other components of the control interface region 282 by a dedicated ground partition.

Figure 13:
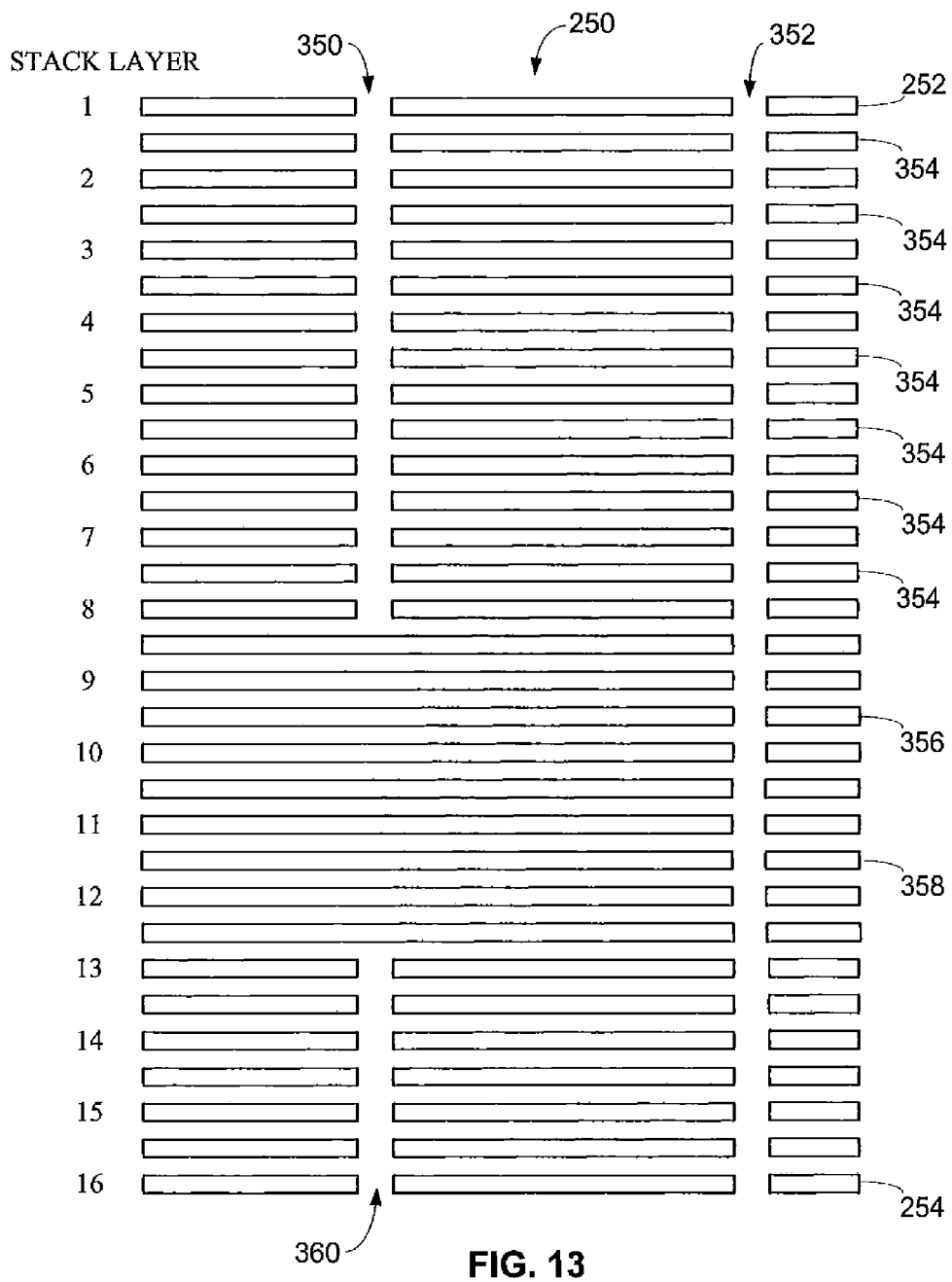
FIG. 13 is an exploded, schematic view of a plurality of layers of a printed circuit board (PCB) assembly according to one embodiment.

The above-described partitioning of the PCB assembly 250 may extend to the power and/or ground planes of the PCB assembly 250. Each power and/or ground plane layer of the PCB assembly 250 may include multiple, discrete plane structures for the above-described regions of the top and bottom PCB layers 252, 254. One or more ground planes configured relative to signal layers of the PCB assembly 250 may connect to one or more power ground planes configured relative to power distribution layers of the PCB assembly 250. Alternatively, only some of the ground plane layers of the PCB assembly 250 include the multiple, discrete ground plane structures. Each ground plane structure may be dedicated to a specific region or region type. In one example, each ground plane layer of the PCB assembly 250 includes respective regional ground plane structures for the analog circuitry, for the digital circuitry, and for the chassis ground. One of the ground plane structures may then be dedicated to supporting the digital devices of the control interface region 282. The other ground plane structure may then be dedicated to supporting the analog circuitry in the detector filter interface region 258, the input buffer amplifier region 260, and the analog region 278. The digital ground plane structure may be configured to support the mixed signal processing region 266. Each of the above-described ground partitions may be coupled to the chassis ground plane structure. In another example, an additional discrete ground plane structure may be dedicated to supporting the mixed signal processing region 276. Examples of such partitioned ground layers of the PCB assembly 250 are schematically shown in FIG. 13.

Figure 11:
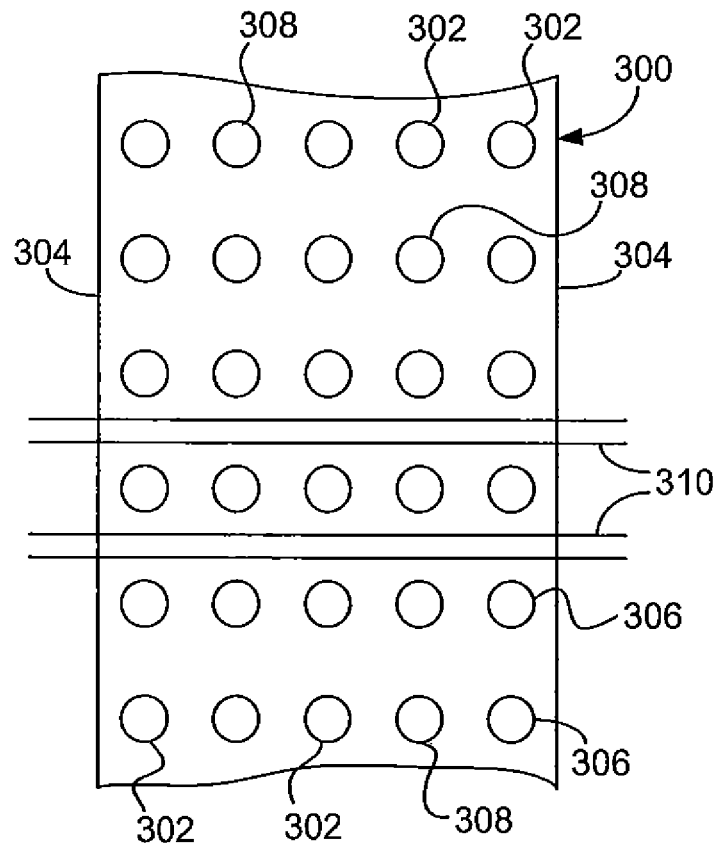
FIG. 11 is a schematic, plan view of a ground partition of a printed circuit board (PCB) assembly according to one embodiment.

FIG. 11 shows one example of a ground partition 300 in greater detail. The ground partition 300 is defined by a plurality of vias 302 that extend through the PCB assembly 250. The vias 302 may extend through one layer, each layer, or a subset of layers, of the PCB assembly 250. At the top PCB layer 252 (FIG. 10A) and the bottom PCB layer 254 (FIG. 10B), the vias 302 may be tied to chassis ground as described herein. The plurality of vias 302 of each ground partition 300 may thus form a wall of chassis ground extending vertically through the PCB assembly 250. Each via 302 may be filled with copper clad or one or more other conductive materials. The vias 302, when taken collectively along one of the ground partitions 300, may minimize the current flowing into or out of a specific circuit or circuit region, such as one of the mixed signal processing quadrants or the control interface.

The plurality of vias 302 may be disposed in a grid pattern to define the length and width of the ground partition 300. The arrangement of the vias 302 may vary from the grid pattern shown, as the vias 302 need not be arranged in columns and rows. The vias 302 may be scattered in a variety of different configurations or arrangements, and need not form a repetitive pattern such as an array. The via arrangement effectively defines longitudinal boundaries 304 of the ground partition 300. The spacing of the longitudinal boundaries 304 defines the width of the ground partition 300.

The size and spacing of the vias 302 may vary across the array. For instance, external vias 306 along the longitudinal boundaries 304 may be larger than internal vias 308 disposed within the perimeter formed by the external vias 306. In one example, each external via 306 has a diameter of 22 mils, while the internal vias have a smaller diameter, e.g., 20 mils. The grid pattern may position the vias 302 with a center-to-center distance of 35 mils in the lateral direction orthogonal to the longitudinal boundaries 304, and 50 mils in the direction parallel to the longitudinal boundaries 304. The external vias 306 may have the same 50 mil pitch in the longitudinal direction, but a varying lateral spacing.

The ground partition 300 may be fabricated by removing solder mask in the area on which the ground partition 300 is formed. The solder mask may be removed via an exposure of 100 mils and a finish of emersion silver or gold flash. Ground planes within the PCB assembly 250 may be filled with conductive material (e.g., copper clad) along the ground partition boundaries 304.

PET detector signals to be processed by the circuitry of the PCB assembly 250 may be routed through the ground partition 300 through respective lateral waveguide apertures 310. As differential signals, the PET detector signals may be routed side-by-side as a differential pair. All of the circuit signals in the PCB assembly 250, both analog and digital, may be differential in structure. One or more signals may single ended or non-differential, such as the single-ended communication signals over the above-described i2C bus. Given the number of differential signals received from the PET detectors, a considerable number of waveguide apertures 310 may pass laterally through the ground partition 300. All of the differential signals need not pass through the ground partition 300 on the same level. The waveguide apertures 310 may be distributed over multiple PCB layers in the PCB assembly 250. The number of waveguide apertures 310 passing laterally through the ground partition 300 may vary given a certain ground partition, the number of PCB layers devoted to signal planes, etc. The ground planes within the PCB assembly 250 along the ground partition 300 may be filled up to the signal spacing limits for routing a trace through the waveguide apertures 310 laterally through the ground partition 300.

The waveguide apertures 310 may be used to allow traces to be formed within the waveguide aperture 310 for carrying PET detector signals from the input filters in the region 258 to the analog input buffer amplifiers in the region 260, crossing the ground partition 256 as shown in FIG. 10A. The waveguide apertures 310 may alternatively pass through the ground partition 268 to allow traces to carry PET detector signals from the analog input buffer amplifiers in the region 260 to the A/D flash amplifiers in the region 266. The waveguide apertures 310 (and the waveguide aperture structure) may be used to pass PET detector signals through any of the ground partitions of the PCB assembly 250.

The waveguide apertures 310 and the ground partition 300 are dimensioned so that EMI in the MR frequency band cannot propagate laterally through the ground partition. For example, the width of the ground partition and the spacing between the vias 302 are selected so that the waveguide apertures 310 prevent signals in the MR frequency band from passing from one circuit or circuit region to a neighboring or adjacent circuit or circuit region.

The spacing between the vias 302 may be adjusted to accommodate some or all of the waveguide apertures 310. For example, one or more of the vias 302 (e.g., rows of vias) may be removed in order to provide sufficient spacing for high voltage signals (e.g., power traces) and to address creepage and clearance concerns.

The ground partition 300 (and one or more of the other ground partitions described herein) may be in electrical communication with chassis ground. The chassis of a DAU may include the housing in which the PCB assembly 250 is disposed, along with any supporting structure, such as a mounting frame. Each DAU housing may define discrete compartments for a number of the circuits and circuit regions described above. The housing may thus include a number of walls, seams, or other dividers that separate a circuit or circuit region from one or more adjacent circuit or circuit regions. These dividers may form internal or external walls of the DAU housing. These dividers may thus be in addition to those walls that define the outer border of the DAU. One or more of these walls, seams, or other dividers may be disposed along a respective one of the above-described ground partitions. Each of these walls, seams, or other dividers may be in contact with the ground partition. In one example, each of these walls, seams, or other dividers are coupled to the ground partition via an EMI gasket.

Figure 12:
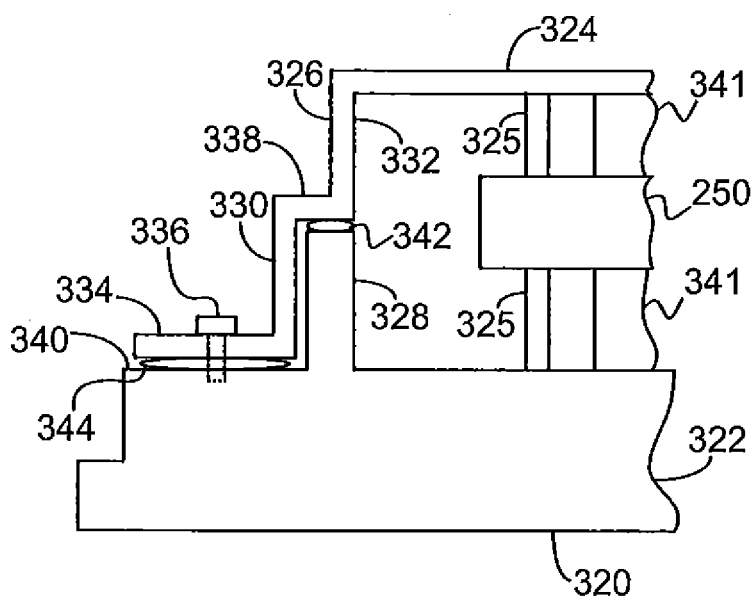
FIG. 12 is a partial, cross-sectional, schematic view of a chassis or housing of a PET data acquisition unit according to one embodiment.

FIG. 12 depicts an EMI gasketing strategy that may be used to provide EMI shielding in conjunction with a DAU housing 320. The EMI strategy incorporates multiple redundancies to minimize EMI emissions and susceptibility. A first redundancy involves overlapping walls at each border or seam. A second redundancy involves multiple EMI gaskets for each seam.

The DAU housing 320 may include a chassis or base 322 and a cover 324. The base 322 and the cover 324 are configured to enclose the PCB assembly 250. The base 322 and the cover 324 may include or support one or more structural components 325, including, for instance, a platform, brace, wall or other structure to support the PCB assembly 250. The structures 325 may act as a mounting frame or other support structure for the DAU. One or more of the structures 325 may be configured as walls that couple the ground partitions of the PCB assembly 250 to chassis ground. The base 322 and/or the cover 324 may have a number of internal or external walls that define a number of compartments, as described above. An external wall 326 of the cover 324 is shown in FIG. 12 as one example. The external wall 326 is stepped to accommodate an upstanding wall 328 that projects upward from the base 322. In this example, the external wall 326 includes a lower section 330 and an upper section 332. The lower section 330 may include a flange 334 to receive one or more bolts or other fasteners 336 for securing the cover 324 to the base 322. The lower section 330 need not be configured as shown, and may thus have other projections or structures configured to couple the base 322 and the cover 324. For instance, the lower section 330 of the wall 326 may include a recessed seat to receive a bolt or other fastener.

The wall 326 is configured to overlap the base 322 in a manner that defines multiple EMI gasket interfaces. In this example, a shoulder 338 of the wall 326 forms a first interface with the base 322 at a top of the wall 328, while the flange 334 forms a second interface with an upper rim 340 of the base 322 beyond the wall 328. The shoulder 338 may form an upper rim that extends laterally outward from the wall 328, running along the perimeter of the housing 320 adjacent to the wall 328. The walls 326 and 328 thus overlap between the two interfaces along the exterior of the housing 320. The wall overlap in this example is formed along the height of the wall 328. Other shoulder arrangements, such as a rim extending inward, may be used.

The PCB assembly 250 may be in thermal communication with the base 322 and/or the cover 324 via one or more thermal gaskets 341. In the example shown, one or more of the thermal gaskets 341 are disposed between each side of the PCB assembly 250 and the base 322 and the cover 324. The thermal gasket(s) 341 may alternatively be disposed between the base 322 and the PCB assembly 250.

Each interface may include respective EMI gasketing. The first interface at the top of the wall 328 includes an EMI gasket 342. The second interface beyond the wall 328 includes an EMI gasket 344. The construction, materials, and other characteristics of the EMI gaskets 342, 344 may vary. In one example, the EMI gaskets 342, 344 include dispensed form-in-place copper filler material commercially available from made by Laird Technologies under model number SNK55-RXP or SNK60-HXP.

The EMI gaskets 342, 344 may run along the exterior of the housing 320 and/or between various housing components (e.g., the housing base 322 and/or the cover 324) and one or more of the ground partitions on the layers 252, 254 of the PCB assembly 250. The EMI gaskets 342, 344 may thus enclose the PCB assembly 250. In one example, the top and bottom layers 252, 254 of the PCB assembly 250 may include a border area adjacent to the EMI gasket 342. The border area may be formed as a ground partition such that the above-described ground partitions are tied to chassis ground as the housing 320 clamps down on the ground partitions.

The redundant shielding provided by the EMI gasket 342 may be useful to provide continuous gasketing along the perimeter of the PCB assembly 250. The protection from the EMI gasket 342 is not interrupted or disturbed by the assembly of the housing 320 due to the absence of any fasteners along the interior gasket 322. In contrast, the EMI gasket 344 is not continuous, as the gasket 344 is pierced by the fasteners 336.

The EMI gasketing strategy may be repeated in connection with a housing for the power filter board (FIG. 5) to the main DAU housing. For example, the power filter housing may be mounted to the cover 324 of the housing 320 such that the cover 324 acts as a base for the power filter housing. The cover 324 may then include a wall similar to the wall 328 to form an overlap with two EMI gasket interfaces, as described above.

One or more EMI gaskets may be provided for any one or more of the internal cavities or compartments of the housing 320. In some embodiments, the DAU includes an EMI gasket for a respective one of the ground partitions that links the ground partition to the housing 320. The housing 320 may not include a wall or other divider disposed upon the ground partition to establish the chassis ground connection, as in the case of the border area of the PCB assembly 250 near an external wall of the housing 320. The EMI gasket may instead link the ground partition to a component of the housing 320. The housing 320 and EMI gasket nonetheless clamp down on the ground partition as the DAU is assembled. For example, the EMI gasket may couple the ground partition to the cover 324. One or more of the ground partitions may thus be in communication with chassis ground. Alternatively, the housing 320 may include a seam, wall or divider along one or more of the ground partitions described above. The divider may be positioned adjacent to the ground partition, with an EMI gasket in between the divider and the ground partition. The divider and EMI gasket then clamp down on the ground partition during assembly. For the ground partitions, the dual strategy is not provided, but may be used in alternative embodiments.

Some of the ground partitions defined on the top PCB layer may not have a housing divider or EMI gasket interface disposed thereon, despite being configured to support such structures. For example, each FPGA may be partitioned from the other devices in the mixed signal processing region via the ground partitions, but not be enclosed in a respective on-board shield provided by, for instance, a discrete housing compartment defined by overlapping walls. The ground partitions may still provide separation through the above-described waveguide apertures to reduce EMI emissions through the PCB assembly 250.

FIG. 13 shows the PCB assembly 250 in greater detail to depict individual PCB layers of the stack according to one embodiment. The PCB assembly 250 may be assembled from multiple sub-assemblies, or subsets of partitioned PCB layers. For example, the PCB assembly 250 may be partitioned into three vertical sections or cores, including a top section (e.g., layers 1-8), a middle section (layers 9-12), and a bottom section (e.g., layers 13-16). The top section may provide interleaved signal and ground planes for the differential signals. The signals may be routed side-by-side as pairs as described above. The middle section may have a number of partitioned dielectric layers for by-passing the top-side circuitry. For example, the middle section may be configured to provide by-pass capacitances formed via two regionally partitioned ceramic dielectric layers. The bottom section may distribute power to local linear regulators and delivers power to the top-side circuits. The bottom layer may also be configured as a thermal gasket interface to the external EMI housing, providing heat sinking to the bottom side regulators as well as heat sinking to top-side circuits through the ground partition vias.

In this example, layer 1 corresponds with the top PCB layer 252, while layer 16 corresponds with the bottom PCB layer 254. Layers 1, 3, 5, and 7 may be configured as ground planes for embedded signal layers 2, 4, 6, and 8. Each ground plane may be formed with 1 oz copper, while each signal layer may have ½ ounce copper. Layers 1-8 are schematically shown with a signal via 350 representative of how the differential signal pairs routed in these layers do not extend the entire depth of the stack, e.g., from the top layer 252 to the bottom layer 254. Layers 2, 4, 6, and 8 carry the interconnects between the above-described devices on the top PCB layer 252 in this embodiment. The RF signals are thus confined to the layers 1-8. Layers 1-8 are also schematically shown with a power via 352 representative of how, in contrast to the signal pairs, power travels the depth of the stack, e.g., from the top layer 252 to the bottom layer 254. Different numbers of ground plane and signal layers may be used. Different via depths may be used based on the signal routing.

Any insulating substrate 354 such as FR-4 may be used to support each of the signal layers and ground layers of the top section of the PCB assembly 250. Each signal layer of the PCB stack is compatible with a variety of dielectric substrate materials. The signal layers are not limited to copper foils.

Beneath the top signal routing section are several layers that form embedded dielectric structures. In this example, layers 9, 10, 11, and 12 may be formed with 1 ounce copper configured as either a power ground plane (layers 9 and 12) or a power plane (layers 10 and 11). A partitioned dielectric layer 356 may be disposed between the planes 9 and 10 and has a thickness to support the formation of embedded capacitors. The partitioned dielectric layer 356 may be a ceramic material. One example of a ceramic dielectric material suitable for the partitioned dielectric layer 356 is "C PLY," which is commercially available from 3M Corporation. Other dielectric materials may be used, including, for example, a thin layer of FR-4 materials (e.g., 50 um). Another C PLY (or other dielectric) layer 358 may be disposed between the planes 11 and 12. Each dielectric layer 356, 358 may be used to form by-pass capacitors for the devices on the top and bottom PCB layers 252, 254. Use of the C PLY-based dielectric layers provides very low inductance capacitance for the by-pass capacitors. The capacitors may be formed between opposed conductor structures formed in the layers adjacent to a respective one of the dielectric layers 356, 358. The bottom PCB layer 254 may include a number of discrete capacitors that work in conjunction with the dielectric layer-based capacitances to provide the by-pass capacitances. Other planes 10 and 11 within the middle dielectric section may be supported by FR-4 or other dielectric substrates.

The bottom section of the PCB assembly 250 may be directed to power distribution and regulation, and disposed on the other side of the dielectric section from the top section. The section may include layers 13-16. In this example, no RF signals are routed through these layers as a result of the vertical partitioning of the PCB assembly 250 in which signal vias do not extend from top to bottom in the PCB stack. Each of layers 13-15 may be formed with 1 ounce copper. Layer 16 may be formed with 2 ounce copper. The thicker copper of the layer 16 may be directed to handling the entire current presented by one or more of the power supplies, which may enter the PCB stack 250 at the layer 16. In one example, four different power buses are brought into the PCB assembly 250, including two digital rails (e.g., digital high and low) and two analog power supply rails (e.g., $+V_A$ and $-V_A$).

The bottom section may be configured to act as a thermal heat sink and thermal gasket interface for conductive heat transfer off of the PCB assembly 250. The bottom section may be in contact with a base, mount, or other structural component of the DAU housing, which, in turn, is in thermal communication with a coolant path as described above. The vias 352 and bottom-section vias 360 may be configured to manage the thermal load presented by the PCB assembly 250. One or more of the vias 352, 360 may be configured as PAD-in-vias.

The above-described DAU board-level partitioning provides integrated and geographically separated shielded structures and thermal management for a number of circuits, including those directed to power distribution and regulation, embedded ceramic dielectrics, mixed-signal circuits (analog to digital converters), and analog circuits. The board-level partitioning limits the EMI emissions from DAU such that operation of 28 housed DAUs, each consuming 100 W of power, have no emissions seeable by the MR system having 32-bit receivers with 140-160 dB of dynamic range.

The disclosed systems may address issues such as thermal management, RF emissions and susceptibility to MR gradient and RF fields for the data processing units (e.g., DAUs) located in the RF cabin. The above-described data processing (or acquisition) units (DAUs) are not limited to use within an RF cabin. The DAUs are well suited for applications or installations in which one or more of the DAUs are located outside of the RF cabin.

MR/PET performance may be improved by locating the DAUs proximate the PET block detectors, not only in the RF cabin, but also along an exterior side or other face of the MR scanner. The lateral side and end face locations of the DAU arrays reduce the PET signal cable length relative to, for example, MR/PET systems in which the digitization occurs outside of the RF cabin. The lateral side and end faces locations may also assist in establishing radial, axial, and other symmetry of the DAU array and/or cabling associated therewith to minimize the impact on MR image quality. PET signal integrity may be improved and potential interoperability issues between the MR and PET DAU may be overcome. Placement of the DAU array in a lateral side region may also minimize the length of the MR scanner (e.g., the MR bore length), while placement of the DAU in an end face location may maintain the form factor of the scanner, each of which may be useful in those installation sites having length or other dimensional restrictions.

The modularity of the disclosed systems may improve manufacturability and serviceability. The disclosed systems may be partitioned or fully assembled and tested as a subsystem prior to integration into the MR cabin. Any combination of one or more of the aspects or embodiments described above may be used.

While the invention has been described above by reference to various embodiments, it should be understood that many changes and modifications can be made without departing from the scope of the invention. For example, the DAUs may be positioned outside the RF cabin. It is therefore intended that the foregoing detailed description be regarded as illustrative rather than limiting, and that it be understood that it is the following claims, including all equivalents, that are intended to define the spirit and scope of this invention.

What is claimed is:

1. An integrated magnetic resonance (MR) and positron emission tomography (PET) system comprising:
    an MR scanner comprising a magnet that defines an opening in which a subject is positioned;
    a set of PET detectors disposed about the opening;
    a plurality of data processing units each electrically connected with a respective one or more of the PET detectors of the set of PET detectors; and
    a plurality of power supply modules, each power supply module being operable to generate a DC power supply for different groups of one or more of the data processing units;
    wherein each power supply module is discrete from the other power supply modules;
    wherein the plurality of data processing units is disposed in an RF cabin in which an MR scanning component is located.

2. The integrated MR and PET system of claim 1, wherein each power supply module of the plurality of power supply modules is configured to provide a high voltage power supply for the one or more of the PET detectors in communication with the respective data processing units.

3. The integrated MR and PET system of claim 1, further comprising a set of power supply hubs, each power supply hub being configured to control a respective array of power supply modules of the plurality of power supply modules.

4. The integrated MR and PET system of claim 3, wherein the set of power supply hubs and the arrays of power supply modules are disposed in a pluggable rack arrangement.

5. The integrated MR and PET system of claim 1, further comprising a plurality of power supply filters disposed at an RF cabin interface, each power supply filter being configured to filter the DC power supply from a respective power supply module of the plurality of power supply modules.

6. The integrated MR and PET system of claim 5, wherein the RF cabin interface includes an access port for a clock signal line for delivering a sine-wave clock to one or more data processing units of the plurality of data processing units.

7. The integrated MR and PET system of claim 5, further comprising respective cabling to carry the DC power supply from each power supply filter of the plurality of power filters to a corresponding data processing unit of the plurality of data processing units, such that distribution of the DC power supplies to the plurality of data processing units has a star configuration.

8. The integrated MR and PET system of claim 7, wherein each data processing unit is galvanically isolated from each of the other data processing units of the plurality of data processing units.

9. The integrated MR and PET system of claim 1, wherein each power supply module is configured as a switch-mode power supply.

10. The integrated MR and PET system of claim 9, wherein each power supply module is phase-locked to a time base of the MR scanner.

11. The integrated MR and PET system of claim 1, further comprising respective cabling to carry the DC power supply, the cabling comprising a twisted-pair conductor for carrying a single-ended power supply, a twisted triplet conductor for carrying a split-rail power supply, and a coax conductor for carrying a high-voltage power supply.

12. The integrated MR and PET system of claim 1, wherein each power supply module is operable to provide low-voltage power configured for operation of one or more of the data processing units.

13. The integrated MR and PET system of claim 1, wherein each power supply module includes a common-mode output filter at an output for the DC power supply.

14. The integrated MR and PET system of claim 1, wherein each power supply module comprises a primary input power circuit breaker switch.

15. An integrated magnetic resonance (MR) and positron emission tomography (PET) system comprising:
   an MR scanner comprising a magnet that defines an opening in which a subject is positioned;
   a set of PET detectors disposed between the magnet and the opening;
   a plurality of data processing units each in communication with a respective one or more of the PET detectors of the set of PET detectors; and
   a power distribution system comprising a plurality of power supply modules, each power supply module being configured to generate a DC power supply for a respective one of the data processing units;
   wherein each data processing unit is in galvanic isolation from each other data processing unit of the plurality of data processing units;
   wherein the plurality of data processing units is disposed in an RF cabin in which an MR scanning component is located.

16. The integrated MR and PET system of claim 15, wherein each power supply module of the plurality of power supply modules is configured to provide a high voltage power supply for the one or more PET detectors in communication with the respective one of the data processing units.

17. The integrated MR and PET system of claim 15, further comprising a set of power supply hubs, each power supply hub being configured to control a respective array of power supply modules of the plurality of power supply modules.

18. The integrated MR and PET system of claim 17, wherein the set of power supply hubs and the arrays of power supply modules are disposed in a pluggable rack arrangement.

19. The integrated MR and PET system of claim 15, further comprising a plurality of power supply filters disposed at an RF cabin interface, each power filter being configured to filter the DC power supply from a respective power supply module of the plurality of power supply modules.

20. The integrated MR and PET system of claim 19, wherein the RF cabin interface includes an access port for a clock signal line for delivering a sine-wave clock to one or more data processing units of the plurality of data processing units.

21. The integrated MR and PET system of claim 19, further comprising respective cabling to carry the DC power supply from each power filter of the plurality of power filters to a corresponding data processing unit of the plurality of data processing units, such that distribution of the DC power supplies to the plurality of data processing units has a star configuration.

22. The integrated MR and PET system of claim 15, wherein each power supply module is configured as a switch-mode power supply.

23. The integrated MR and PET system of claim 22, wherein each power supply module is phase-locked to a time base of the MR scanner.

24. The integrated MR and PET system of claim 15, further comprising respective cabling to carry the DC power supply, the cabling comprising a twisted-pair conductor for carrying a single-ended power supply, a twisted triplet conductor for carrying a split-rail power supply, and a coax conductor for carrying a high-voltage power supply.

25. The integrated MR and PET system of claim 15, wherein each power supply module is operable to provide low-voltage power configured for operation of one or more of the data processing units.

26. The integrated MR and PET system of claim 15, wherein each power supply module includes a common-mode output filter at an output for the DC power supply.

27. The integrated MR and PET system of claim 15, wherein each power supply module comprises a primary input power circuit breaker switch.

28. A method of integrating magnetic resonance (MR) and positron emission tomography (PET) imaging, the method comprising:
   generating a respective DC power supply for each PET data processing unit of a plurality of PET data processing units disposed in an RF cabin in which an MR scanning component is located;
   filtering each DC power supply with a respective power filter of a plurality of power filters disposed at an interface to the RF cabin;
   carrying each filtered DC power supply in the RF cabin to a respective PET data processing unit of the plurality of PET data processing units.

29. The method of claim 28, further comprising further filtering each DC power supply at each PET data processing unit to remove MR noise from the DC power supply.

30. The method of claim 28, further comprising:
   generating a respective high voltage power supply to be delivered to one or more PET detectors in communication with each PET data processing unit; and carrying the high voltage power supply via respective cabling in which the filtered DC power supply is carried.

31. The method of claim 28, wherein each power filter is a common-mode output filter.

32. The method of claim 28, further comprising delivering a sine-wave clock to each PET data processing unit via the interface to the RF cabin.

* * * * *